US008414587B2

(12) United States Patent
Saal et al.

(10) Patent No.: US 8,414,587 B2
(45) Date of Patent: Apr. 9, 2013

(54) STYLI USED TO POSITION DEVICE FOR CARRYING OUT SELECTIVE DISCETOMY

(75) Inventors: Jeffrey Alan Saal, Portola Valley, CA (US); Joel Stuart Saal, Portola Valley, CA (US); Brian R. Dubois, Redwood City, CA (US); Jeff Christian, Morgan Hill, CA (US)

(73) Assignee: Laurimed, LLC, Redwood City, CA (US)

( * ) Notice: Subject to any disclaimer, the term of this patent is extended or adjusted under 35 U.S.C. 154(b) by 1196 days.

(21) Appl. No.: 11/848,562

(22) Filed: Aug. 31, 2007

(65) Prior Publication Data

US 2008/0183175 A1  Jul. 31, 2008

Related U.S. Application Data

(60) Provisional application No. 60/886,860, filed on Jan. 26, 2007, provisional application No. 60/887,997, filed on Feb. 2, 2007, provisional application No. 60/892,498, filed on Mar. 1, 2007, provisional application No. 60/896,226, filed on Mar. 21, 2007, provisional application No. 60/945,521, filed on Jun. 21, 2007, provisional application No. 60/945,518, filed on Jun. 21, 2007, provisional application No. 60/945,519, filed on Jun. 21, 2007.

(51) Int. Cl.
A61B 17/00 (2006.01)

(52) U.S. Cl.
USPC .......................................................... 606/84

(58) Field of Classification Search .......... 606/79, 606/80, 81, 84, 85, 167, 170, 180; 623/17.11–17.16
See application file for complete search history.

(56) References Cited

U.S. PATENT DOCUMENTS

| 1,527,291 A | 2/1925 | Zorraquin |
| 1,733,502 A | 10/1929 | Linsley |
| 2,895,455 A | 7/1959 | Clowes |

(Continued)

FOREIGN PATENT DOCUMENTS

| RU | 2029533 | 2/1995 |
| WO | WO 2008/094444 | 8/2008 |

(Continued)

OTHER PUBLICATIONS

Sice et al, "Epidural analgesia after spinal surgery via intervertebral foramen," *British Journal of Anaesthesia*, 94(3), pp. 378-380, Dec. 24, 2004.

*Primary Examiner* — Kevin T Truong
*Assistant Examiner* — Christopher Beccia
(74) *Attorney, Agent, or Firm* — Levine Bagade Han LLP

(57) ABSTRACT

A set of styli comprised of a shaped memory or elastic metal are disclosed wherein each stylus has a different preformed curvatures for use with a cutting device for performing a selective discectomy. The device is inserted at a point chosen from contralateral, anterior or anterolateral relative to a herniation site. Once the cutting device is inserted its cutting window is moved to the desired position by inserting a first stylus having an appropriate curvature and moving the device, removing the stylus, inserting a second stylus with a different curvature relative to the first stylus before or after moving the device. By using a plurality of styli with different curvatures and using positioning movements the cutting window is positioned at the site of herniation and a selective discectomy is carried out.

35 Claims, 9 Drawing Sheets

U.S. PATENT DOCUMENTS

| | | |
|---|---|---|
| 3,081,770 A | 3/1963 | Hunter |
| 3,469,580 A | 9/1969 | Huddy |
| 3,682,162 A | 8/1972 | Colyer |
| 3,689,955 A | 9/1972 | Winkelmann |
| 3,709,211 A | 1/1973 | Hawkins |
| 3,782,381 A | 1/1974 | Winnie |
| 3,815,604 A | 6/1974 | O'Malley et al. |
| 3,884,238 A | 5/1975 | O'Malley et al. |
| 3,941,127 A | 3/1976 | Froning |
| 3,943,932 A | 3/1976 | Woo |
| 3,977,400 A | 8/1976 | Moorehead |
| 4,013,080 A | 3/1977 | Froning |
| 4,068,659 A | 1/1978 | Moorehead |
| 4,192,319 A | 3/1980 | Hargens et al. |
| 4,314,560 A | 2/1982 | Helfgott et al. |
| RE30,966 E | 6/1982 | Hargens et al. |
| 4,349,023 A | 9/1982 | Gross |
| 4,368,730 A | 1/1983 | Sharrock |
| 4,507,167 A | 3/1985 | Jahme et al. |
| 4,511,356 A | 4/1985 | Froning et al. |
| 4,580,573 A | 4/1986 | Quinn |
| 4,588,399 A | 5/1986 | Nebergall et al. |
| 4,609,370 A | 9/1986 | Morrison |
| 4,662,869 A | 5/1987 | Wright |
| 4,678,459 A * | 7/1987 | Onik et al. ............... 604/22 |
| 4,721,506 A | 1/1988 | Teves |
| 4,737,146 A | 4/1988 | Amaki et al. |
| 4,775,637 A | 10/1988 | Sutherland et al. |
| 4,808,157 A | 2/1989 | Coombs |
| 4,842,585 A | 6/1989 | Witt |
| 4,846,799 A | 7/1989 | Tanaka et al. |
| 4,886,067 A | 12/1989 | Palermo |
| 4,917,668 A | 4/1990 | Haindl |
| 4,917,670 A | 4/1990 | Hurley et al. |
| RE33,258 E | 7/1990 | Onik et al. |
| 4,940,458 A | 7/1990 | Cohn |
| 4,958,901 A | 9/1990 | Coombs |
| 4,973,305 A | 11/1990 | Goltzer |
| 4,973,312 A | 11/1990 | Andrew |
| 4,994,036 A | 2/1991 | Biscoping et al. |
| 5,004,456 A | 4/1991 | Botterbusch et al. |
| 5,007,902 A | 4/1991 | Witt |
| 5,024,655 A | 6/1991 | Freeman et al. |
| 5,026,350 A | 6/1991 | Tanaka et al. |
| 5,078,679 A | 1/1992 | Reese |
| 5,085,631 A | 2/1992 | Leighton |
| 5,098,388 A | 3/1992 | Kulkashi et al. |
| 5,100,379 A | 3/1992 | Wendell |
| 5,100,390 A | 3/1992 | Lubeck et al. |
| 5,106,376 A | 4/1992 | Mononen et al. |
| 5,119,832 A | 6/1992 | Xavier |
| 5,129,889 A | 7/1992 | Hahn et al. |
| 5,135,525 A | 8/1992 | Biscoping et al. |
| 5,160,323 A | 11/1992 | Andrew |
| 5,163,901 A | 11/1992 | Eldor |
| 5,205,828 A | 4/1993 | Kedem |
| 5,207,647 A | 5/1993 | Phelps |
| 5,209,734 A | 5/1993 | Hurley et al. |
| 5,213,578 A | 5/1993 | Heiliger et al. |
| 5,232,442 A | 8/1993 | Johnson et al. |
| 5,234,406 A | 8/1993 | Drasner et al. |
| 5,257,972 A | 11/1993 | Gurmarnik |
| 5,263,936 A | 11/1993 | Yurino |
| 5,269,769 A | 12/1993 | Dhara et al. |
| 5,292,310 A | 3/1994 | Yoon |
| 5,304,141 A | 4/1994 | Johnson et al. |
| 5,306,239 A | 4/1994 | Gurmarnik et al. |
| 5,312,374 A | 5/1994 | Gurmarnik |
| 5,312,375 A | 5/1994 | Gurmarnik |
| 5,320,610 A | 6/1994 | Yoon |
| 5,328,479 A | 7/1994 | Gurmarnik |
| 5,335,671 A | 8/1994 | Clement |
| 5,368,573 A | 11/1994 | Andrew |
| 5,376,082 A | 12/1994 | Phelps |
| 5,385,561 A | 1/1995 | Cerny |
| 5,392,790 A | 2/1995 | Kanner et al. |
| 5,405,334 A | 4/1995 | Roth et al. |
| 5,417,208 A | 5/1995 | Winkler |
| 5,423,760 A | 6/1995 | Yoon |
| 5,423,770 A | 6/1995 | Yoon |
| 5,425,717 A | 6/1995 | Mohiuddin |
| 5,449,351 A | 9/1995 | Zohmann |
| 5,470,318 A | 11/1995 | Griffith, III et al. |
| 5,480,389 A | 1/1996 | McWha et al. |
| 5,490,845 A | 2/1996 | Racz |
| 5,512,045 A | 4/1996 | Gurchumelidze |
| 5,512,052 A | 4/1996 | Jesch |
| 5,520,652 A | 5/1996 | Peterson |
| 5,542,918 A | 8/1996 | Atkinson |
| 5,569,178 A | 10/1996 | Henley |
| 5,573,519 A | 11/1996 | Zohmann |
| 5,584,820 A | 12/1996 | Gurmarnik |
| 5,591,132 A | 1/1997 | Carrie |
| 5,611,778 A | 3/1997 | Brinon |
| 5,628,734 A | 5/1997 | Hatfalvi |
| 5,630,802 A | 5/1997 | Moellmann et al. |
| 5,637,096 A | 6/1997 | Yoon |
| 5,669,876 A | 9/1997 | Schechter et al. |
| 5,669,882 A | 9/1997 | Pyles |
| 5,672,158 A | 9/1997 | Okada et al. |
| 5,685,852 A | 11/1997 | Turkel et al. |
| 5,725,504 A | 3/1998 | Collins |
| 5,730,754 A | 3/1998 | Obenchain |
| 5,752,969 A | 5/1998 | Cunci et al. |
| 5,779,666 A | 7/1998 | Teirstein |
| 5,779,680 A | 7/1998 | Yoon |
| 5,820,588 A | 10/1998 | Howard, III |
| 5,830,188 A | 11/1998 | Abouleish |
| 5,833,662 A | 11/1998 | Stevens |
| 5,836,914 A | 11/1998 | Houghton |
| 5,836,916 A | 11/1998 | Corn |
| 5,846,226 A | 12/1998 | Urmey |
| 5,853,391 A | 12/1998 | Bell |
| 5,857,996 A | 1/1999 | Snoke |
| 5,871,470 A | 2/1999 | McWha |
| 5,885,217 A | 3/1999 | Gisselberg et al. |
| 5,899,891 A | 5/1999 | Racz |
| 5,941,853 A | 8/1999 | Collins |
| 5,957,881 A | 9/1999 | Peters et al. |
| 5,976,110 A | 11/1999 | Greengrass et al. |
| 6,004,293 A | 12/1999 | Bell |
| 6,068,642 A | 5/2000 | Johnson et al. |
| 6,095,149 A | 8/2000 | Sharkey et al. |
| 6,113,569 A | 9/2000 | Becker |
| 6,179,828 B1 | 1/2001 | Mottola et al. |
| 6,190,370 B1 | 2/2001 | Tsui |
| 6,193,704 B1 | 2/2001 | Winters |
| 6,221,048 B1 | 4/2001 | Phelps |
| 6,245,044 B1 | 6/2001 | Daw et al. |
| 6,273,873 B1 | 8/2001 | Fleischer |
| 6,296,624 B1 | 10/2001 | Gerber et al. |
| 6,298,256 B1 | 10/2001 | Meyer |
| 6,363,273 B1 | 3/2002 | Mastrorio et al. |
| 6,371,943 B1 | 4/2002 | Racz et al. |
| 6,558,353 B2 | 5/2003 | Zohmann |
| 6,572,593 B1 | 6/2003 | Daum |
| 6,592,559 B1 | 7/2003 | Pakter et al. |
| 6,610,066 B2 | 8/2003 | Dinger et al. |
| 6,620,180 B1 | 9/2003 | Bays et al. |
| 6,638,238 B1 | 10/2003 | Weber et al. |
| 6,641,563 B1 | 11/2003 | Vitullo et al. |
| 6,708,489 B2 | 3/2004 | Massey et al. |
| 6,709,418 B1 | 3/2004 | Aboul-Hosn et al. |
| 6,764,491 B2 | 7/2004 | Frey et al. |
| 6,899,712 B2 | 5/2005 | Moutafis et al. |
| 6,923,813 B2 | 8/2005 | Phillips et al. |
| 6,925,333 B2 | 8/2005 | Krebs |
| 6,979,317 B2 | 12/2005 | Galt et al. |
| 7,022,109 B1 | 4/2006 | Ditto |
| 7,120,487 B2 | 10/2006 | Nelson |
| 7,181,289 B2 | 2/2007 | Pflueger et al. |
| 7,234,468 B2 | 6/2007 | Johnson et al. |
| 7,244,263 B2 * | 7/2007 | Robison et al. ............... 606/170 |
| 7,318,831 B2 | 1/2008 | Alvarez et al. |
| 7,400,930 B2 | 7/2008 | Sharkey et al. |
| 7,465,278 B2 | 12/2008 | Cicenas et al. |
| 7,632,294 B2 * | 12/2009 | Milbodker et al. ............... 606/279 |

| | | | |
|---|---|---|---|
| 7,647,123 B2 * | 1/2010 | Sharkey et al. ............... 607/117 | |
| 7,727,186 B2 | 6/2010 | Makower et al. | |
| 7,740,631 B2 * | 6/2010 | Bleich et al. .................... 606/79 | |
| 7,806,834 B2 | 10/2010 | Beckman et al. | |
| 7,819,819 B2 | 10/2010 | Quick et al. | |
| 7,828,748 B2 | 11/2010 | Hibner | |
| 7,854,706 B2 | 12/2010 | Hibner | |
| 7,909,822 B2 | 3/2011 | Guerra | |
| 7,918,804 B2 | 4/2011 | Monson et al. | |
| 8,016,846 B2 | 9/2011 | McFarlin et al. | |
| 8,088,119 B2 | 1/2012 | Saal et al. | |
| 2002/0183758 A1 | 12/2002 | Middleton et al. | |
| 2003/0176778 A1 | 9/2003 | Messing et al. | |
| 2003/0212395 A1 | 11/2003 | Woloszko et al. | |
| 2004/0034339 A1 | 2/2004 | Stoller et al. | |
| 2004/0049217 A1 | 3/2004 | Ross et al. | |
| 2004/0064127 A1 | 4/2004 | Lerner | |
| 2004/0092992 A1 | 5/2004 | Adams et al. | |
| 2004/0098006 A1 | 5/2004 | Nakanishi | |
| 2004/0102760 A1 | 5/2004 | Hsue et al. | |
| 2004/0127963 A1 * | 7/2004 | Uchida et al. .................... 607/96 | |
| 2004/0210231 A1 | 10/2004 | Boucher et al. | |
| 2004/0267282 A1 | 12/2004 | Shkarubo et al. | |
| 2005/0004563 A1 | 1/2005 | Racz et al. | |
| 2005/0010205 A1 * | 1/2005 | Hovda et al. .................... 606/41 | |
| 2005/0090801 A1 | 4/2005 | Racz et al. | |
| 2005/0197661 A1 | 9/2005 | Carrison et al. | |
| 2005/0203527 A1 * | 9/2005 | Carrison et al. ............... 606/80 | |
| 2005/0234425 A1 | 10/2005 | Miller et al. | |
| 2005/0261692 A1 | 11/2005 | Carrison et al. | |
| 2006/0004369 A1 * | 1/2006 | Patel et al. ....................... 606/79 | |
| 2006/0064101 A1 * | 3/2006 | Arramon ......................... 606/82 | |
| 2006/0110017 A1 | 5/2006 | Tsai et al. | |
| 2006/0111728 A1 | 5/2006 | Abdou | |
| 2006/0129062 A1 | 6/2006 | Nicoson et al. | |
| 2006/0229550 A1 | 10/2006 | Staid et al. | |
| 2006/0239982 A1 | 10/2006 | Simpson | |
| 2006/0258951 A1 | 11/2006 | Bleich et al. | |
| 2006/0264994 A1 | 11/2006 | Schomer et al. | |
| 2006/0271196 A1 | 11/2006 | Saal et al. | |
| 2006/0271197 A1 | 11/2006 | Saal et al. | |
| 2006/0284994 A1 | 12/2006 | Kim | |
| 2007/0055259 A1 | 3/2007 | Norton et al. | |
| 2007/0162062 A1 | 7/2007 | Norton et al. | |
| 2008/0183175 A1 | 7/2008 | Saal et al. | |
| 2008/0183192 A1 | 7/2008 | Saal et al. | |
| 2008/0188826 A1 | 8/2008 | Saal | |
| 2008/0188827 A1 | 8/2008 | Saal | |
| 2008/0221586 A1 | 9/2008 | Garcia-Bengochea et al. | |
| 2008/0221589 A1 | 9/2008 | Balling et al. | |
| 2008/0221605 A1 | 9/2008 | Saal et al. | |
| 2008/0255563 A1 | 10/2008 | Farr et al. | |
| 2008/0294166 A1 | 11/2008 | Goldin et al. | |
| 2008/0294167 A1 | 11/2008 | Schumacher et al. | |
| 2009/0048678 A1 | 2/2009 | Saal et al. | |
| 2009/0076486 A1 | 3/2009 | Cucin | |
| 2009/0216234 A1 | 8/2009 | Farr et al. | |
| 2009/0259126 A1 | 10/2009 | Saal et al. | |
| 2010/0152611 A1 | 6/2010 | Parihar et al. | |
| 2011/0054349 A1 | 3/2011 | Hibner | |
| 2011/0098596 A1 | 4/2011 | Ozturk et al. | |
| 2011/0306879 A1 | 12/2011 | Saal et al. | |
| 2012/0004595 A1 | 1/2012 | DuBois et al. | |

FOREIGN PATENT DOCUMENTS

| | | |
|---|---|---|
| WO | WO 2008/099436 | 8/2008 |
| WO | WO 2008/094439 | 9/2008 |
| WO | WO 2008/095177 | 10/2008 |
| WO | WO 2009/052194 | 4/2009 |
| WO | WO 2009/124192 | 10/2009 |
| WO | WO 2012/003383 | 1/2012 |

* cited by examiner

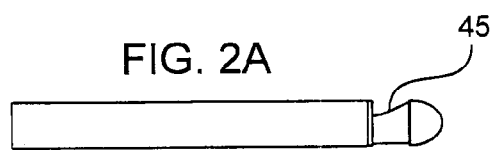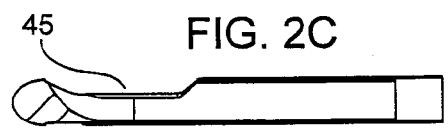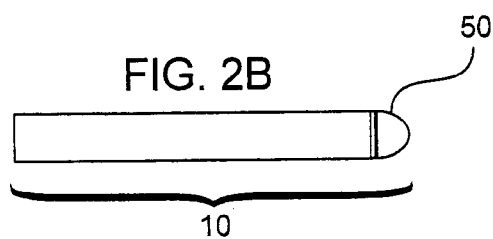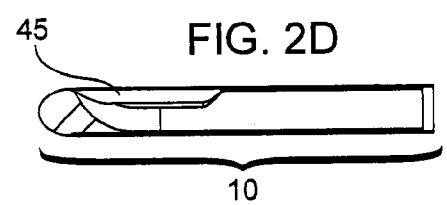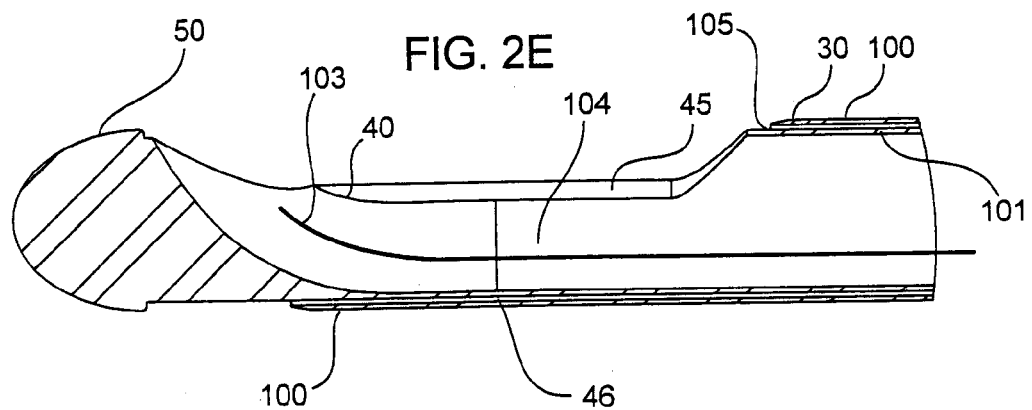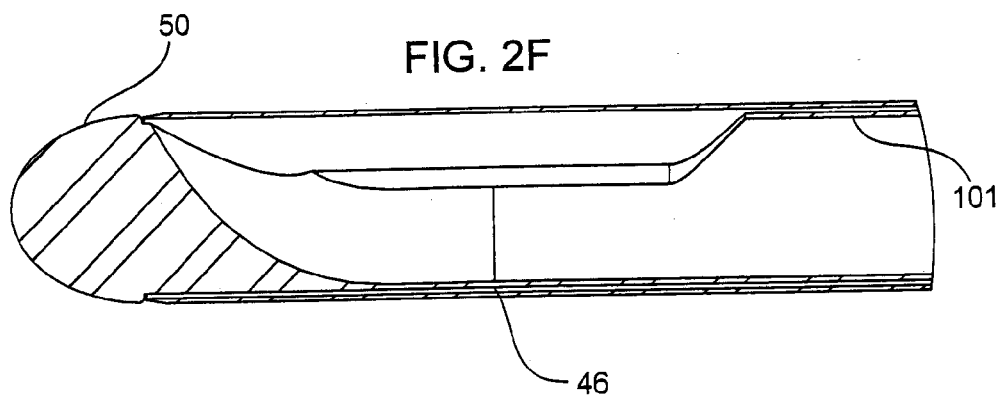

STYLI USED TO POSITION DEVICE FOR CARRYING OUT SELECTIVE DISCETOMY

CROSS-REFERENCE

This application claims the benefit of U.S. Provisional Application Nos. 60/886,860, filed Jan. 26, 2007; 60/887,997, filed Feb. 2, 2007; 60/892,498, filed Mar. 1, 2007; 60/896,226, filed Mar. 21, 2007; 60/945,521, filed Jun. 21, 2007; 60/945,518, filed Jun. 21, 2007; and 60/945,519, filed Jun. 21, 2007, which applications are incorporated herein by reference. This application further incorporates by reference patent applications filed on the same day herewith.

FIELD OF THE INVENTION

The present invention is drawn to a flexible surgical cutting device which is navigable within a subject such as within the confines of the intervertebral disc and methods of using the subject devices for performing selective percutaneous discectomy.

BACKGROUND OF THE INVENTION

The intervertebral disc is composed of a thick outer ring of cartilage (annulus) and an inner gel-like substance (nucleus pulposus). The annulus contains collagen fibers that form concentric lamellae that surround the nucleus and insert into the endplates of the adjacent vertebral bodies. The nucleus pulposus comprises proteoglycans entrapped by a network of collagen and elastin fibers which has the capacity to bind water. When healthy, the intervertebral disc keeps the spine flexible and serves as a shock absorber by allowing the body to accept and dissipate loads across multiple levels in the spine.

Over time, the nucleus pulposus becomes less fluid and more viscous as a result of age, normal wear and tear, and damage caused from an injury. The proteoglycan and water from within the nucleus decreases which in turn results in the nucleus drying out and becoming smaller and compressed. Additionally, the annulus tends to thicken, desiccate, and become more rigid, lessening its ability to elastically deform under load and making it susceptible to disc fissures.

A fissure occurs when the fibrous components of the annulus become separated in particular areas, creating a tear within the annulus. The most common type of fissure is a radial fissure in which the tear is perpendicular to the direction of the fibers. A fissure associated with disc herniation generally falls into three types of categories: 1) contained disc herniation (also known as contained disc protrusion); 2) extruded disc herniation; and 3) sequestered disc herniation (also known as a free fragment.)

In a contained herniation, a portion of the disc protrudes or bulges from a normal boundary of the disc but does not breach the outer annulus fibrosis. In an extruded herniation, the annulus is disrupted and a segment of the nucleus protrudes/extrudes from the disc. However, in this condition, the nucleus within the disc remains contiguous with the extruded fragment. With a sequestered disc herniation, a nucleus fragment separates from the nucleus and disc.

As the posterior and posterolateral portions of the annulus are most susceptible to herniation, in many instances, the nucleus pulposus progresses into the fissure from the nucleus in a posteriorly or posterolateral direction. Additionally, biochemicals contained within the nucleus pulposus may escape through the annulus causing inflammation and irritating adjacent nerves. Symptoms of a herniated disc generally include sharp back or neck pain which radiates into the extremities, numbness, muscle weakness, and in late stages, paralysis, muscle atrophy and bladder and bowel incontinence.

Conservative therapy is the first line of treating a herniated disc which includes bed rest, medications to reduce inflammation and pain, physical therapy, patient education on proper body mechanics and weight control.

However, if conservative therapy offers no improvement then surgery is recommended. Open discectomy is the most common surgical treatment for ruptured or herniated discs. The procedure involves an incision in the skin over the spine to remove the herniated disc material so it no longer presses on the nerves and spinal cord. Before the disc material is removed, some of the bone from the affected vertebra may be removed using a laminotomy or laminectomy to allow the surgeon to better see the area.

However, minimally invasive techniques have been rapidly replacing open surgery in treating herniated discs. Minimally invasive surgery utilizes small skin incisions, thereby minimizing the damaging effects of large muscle retraction and offering rapid recovery, less post-operative pain and small incisional scars. Examples of well-known minimally invasive techniques are provided below.

Microdiscectomy employs a surgical microscope and microsurgical techniques to view the disc and nerves. The magnified view makes it possible for the surgeon to remove only the herniated disc material which is "pinching" one or more spinal nerve root through a smaller incision, thus causing less damage to surrounding tissue.

Percutaneous discectomy uses a needle-like device which enters the disc space posterolaterally to remove the herniated disc material in a piecemeal fashion. Examples of such devices are described in U.S. Pat. No. 4,678,459. Using suction to pull in disc material, these cutting devices use a slide-like motion to slice the tissue which is then aspirated to a collection bottle. However, as illustrated in FIGS. 1A and 1B, these prior art devices are typically rigid and therefore, only able to access the center of the nucleus and remove material along a linear path from the access point to the center of the nucleus (1). As a result, the tissue removal is not performed at the site of the injury and thereby has limited effectiveness. Furthermore, the rigid devices are typically able to treat only the L4-L5 disc and not the L5-S1 disc that is commonly the source of patient discomfort. The L5-S1 disc is the lowest disc on the spine and because it is below the iliac crest, it is accessible by approaching it from an angle of approximately 30 degrees above the plane of the disc. A rigid device cannot access the disc unless it can approach the disc from within the same plane as the disc.

Endoscopic discectomy inserts an endoscopic probe between the vertebrae and into the herniated disc space through the skin of the back using an x-ray video image for guidance. Surgical attachments (cutters, lasers, and the like) are then sent down the hollow center of the probe to remove a portion of the offending disc. However, this direct approach to the disc herniation results in further injury to the already weakened disc annulus, thereby increasing the likelihood of subsequent herniations. Sometimes, the surgical attachments can be used to push the bulging disc back into place and for the removal of disc fragments and small bone spurs. The surgeon introduces the endoscope through a relatively large, (approximately 10 mm or greater), incision into the skin above the spine, then locates the nerve and disc using direct visualization.

Chemonucleolysis involves the injection of chymopapain or other nucleus dissolving substance into the disc to partially dissolve the nucleus to alleviate disc herniation. Chymopapain is an enzyme that works by depolymerizing the proteoglycan and glycoprotein molecules in the nucleus pulposus. These large molecules are responsible for water retention and turgidity. When exposed to chymopapain, the water content within the disc decreases resulting in shrinkage, thereby causing a reduction in disc height and girth.

Nucleoplasty involves the percutaneous removal of disc material by using a low-temperature resister probe to disintegrate and evacuate disc material, followed by thermal treatment of adjacent residual disc material. The procedure combines disc removal and thermal coagulation to putatively decompress a contained herniated disc. A posterolateral approach is guided by fluoroscopy and a discogram may take place at this time to confirm location. Taking care not to contact the anterior annulus, the nucleus pulposus is first ablated with radiofrequency waves as the wand is advanced causing a molecular dissociation process converting tissue into gas which putatively escapes through the needle. As the wand is withdrawn, coagulation takes place thermally treating the channel, which leads to a denaturing of nerve fibers adjacent to the channel within the nucleus pulposus.

Intradiscal electrothermal therapy involves the percutaneous insertion of a specially designed thermal resistance probe followed by controlled heating of the intervertebral disc. This may result in limited annulus contraction and coagulation of nerve tissue and reduction in pain. A needle is inserted posterolaterally into the disc, generally from the patient's less painful side. A cannula with a flexible heating tip is threaded circumferentially into the disc through the nucleus pulposus to the pathologic area of the annulus.

Percutaneous Laser Discectomy involves directing a laser to the target tissue area which absorbs the laser light and converts it to heat. When the temperature reaches 100° C., tissue vaporizes and ablation takes places. As a small amount of nucleus pulposus is vaporized, intradiscal pressure decreases, allowing the disc to return to its normal state.

The above methods typically employ a posterior lateral approach for accessing the nucleus. This approach relies on a rigid introducer to pierce through the annulus and access the nucleus pulposus. Generally only the center or anterior portion of the nucleus is accessible with these methods because of the entry angle and density of the nucleus. However, most herniations typically occur in the posterior portion because the posterior wall of the annulus is thinner than the anterior wall. Therefore, the above methods are unable to access and treat most herniations at the specific site of injury.

Additionally, the above methods are based on the concept in which the intervertebral disc acts as a closed hydraulic system. According to this theory, the nucleus pulposus contains a large amount of water and is surrounded by the inelastic annulus fibrosis. Therefore, disc pressure decreases by removing nucleus pulposus material from the center of the nucleus which causes the herniated disc material to recede toward the center of the disc. As such, the above methods are designed to merely remove a portion of the nucleus pulposus within the center of the nucleus but do not specifically remove material from within the site of injury.

In light of the foregoing discussion, there is a need for a device that allows for active and directional navigation within the confines of the disc to directly access the injured disc material at the site of herniation. In particular, there is a need for a device that can navigate within the nucleus pulposus and excise material directly from the site of herniation within the fissure.

SUMMARY OF THE INVENTION

An aspect of the invention is a method for navigating a cutting device to treat a disc herniation within an intervertebral disc, carried out by introducing a cutting device into an intervertebral disc wherein the device enters the nucleus contralateral or anterolateral to a herniation site, and moving a cutting component of the device to the herniation site by sequentially inserting styli with different radii of curvature relative to each other. The device can enter the disc anterior or anterolateral relative to the site of herniation. The method may be carried out by having the cutting device introduced to the nucleus by a cannula inserted into a patient at a point contralateral or anterolateral to the herniation site. The cutting device may be introduced to the nucleus of the intervertebral disc at a posterolateral extrapedicular point. The method may also include cutting nucleus pulposus material away from within the nucleus at the site of herniation, and removing nucleus pulposus material cut away from the nucleus at the site of herniation. To improve accuracy the method may include visualizing the cutting device in the nucleus, and using the visualization to position the cutting component at the site of herniation.

Another aspect of the invention is a method for navigating a cutting device within an intervertebral disc, carried out by introducing into the intervertebral disc, a cutting device positioned at a distal end of a flexible shaft, adjusting a curvature of a distal portion of the shaft while the cutting device is within the intervertebral disc space, positioning a cutting window on the cutting device in an area of a diagnosed herniation, and inserting a stylus with a distal end portion with a predetermined curvature into the shaft. The method may be carried out wherein the adjusting is carried out by inserting a stylus into the device that has a radius of curvature that is different from the radius of curvature of the distal portion of the device wherein the stylus is comprised of a shaped memory or elastic metal. The method can include removing the stylus from the shaft, and beginning a debulking process.

Another aspect of the invention is a method for navigating a cutting device within an intervertebral disc, by introducing into an intervertebral disc, a cutting device positioned at a distal end of a flexible shaft, adjusting a curvature of a distal portion of the shaft while the cutting device is within the intervertebral disc space, and positioning a cutting window on the device in an area of a diagnosed herniation. This method may be carried out by adjusting of the shaft curvature by inserting a first stylus into the device which first stylus has a first predetermined curvature at its distal end, causing the cutting device to change position, inserting a second stylus with a second predetermined curvature at its distal end which second curvature is different from the first curvature, and again causing the cutting device to change position. In the method the first and second stylus may each be comprised of a shaped memory or elastic metal.

Still another aspect of the invention is a method for navigating a cutting device within an intervertebral disc, by introducing into said intervertebral disc, a cutting device positioned at a distal end of a flexible shaft, adjusting a curvature of a distal portion of the shaft while the cutting device is within the intervertebral disc space, and positioning a cutting window on the cutting device in an area of a diagnosed herniation, wherein the adjusting is carried out by using a plurality of styli with different radii of curvature.

An aspect of the invention is a cutting device for performing a selective discectomy, comprising a flexible outer shaft comprising a distal end, a flexible inner shaft inserted within the outer shaft and comprising a distal end wherein distal end portions of the outer and inner shafts are configured to interact and provide for cutting, and a stylus comprised of shaped memory or elastic material with a predetermined radius of curvature, the stylus being inserted into the device to change the outer and inner shaft curvature. The device may be comprised wherein the stylus is partially encapsulated by a sheath that changes a radius of curvature of the stylus and further wherein a distal portion of the device is adjustable to curve a distal portion of the outer shaft and inner shaft.

Another aspect of the invention is a cutting device for performing a selective discectomy, which includes a shaft comprising a cutting mechanism at a distal end, and a stylus comprised of a shaped memory or elastic material with a predetermined radius of curvature at its distal end inserted into the shaft.

Still another aspect of the invention is a cutting device system for performing a selective discectomy, that includes a shaft comprising a cutting mechanism at a distal end of the shaft, and a plurality of styli in a set, wherein a stylus in the set is comprised of shaped memory or elastic metal that is of a different radius of curvature relative to another stylus in the set.

The device may include a cutting window at a distal end of the shaft. The device may further include a plurality of styli of a set partially encapsulated by a sheath that changes a radius of curvature of the stylus.

While carrying out the method of the invention the device is within the intervertebral disc. Thus, the invention includes a disc comprising a nucleus, a diagnosed site of herniation positioned at a first side of the nucleus, and a flexible shaft comprising a cutting component at a distal end of the shaft, the shaft inserted into the nucleus at a second side contralateral or anterolateral to the first side and positioned with the cutting component adjacent the diagnosed site of herniation. The intervertebral disc may have therein a stylus having a predetermined curvature inserted into the shaft.

The present invention is drawn to a flexible surgical cutting device and methods of use. The device is comprised of an outer shaft which at its distal end is positioned a cutting tool which is in the form of a circular distal end on the outer circumference of the shaft which distal end includes a sharp edge. An inner shaft may be solid and move slidably inside the outer shaft. The inner shaft comprises a window or opening on a side of a distal end portion. A safety tip is positioned at a distal end of the distal end portion of the inner shaft. The device is inserted into a subject contralateral or anterolateral to the point of disc herniation and the window or opening is positioned near disc material (e.g. the herniation) targeted for removal. By applying vacuum the material is sucked into the anvil window. The outer shaft is moved in a direction such that the cutter on the distal end of the outer shaft is advanced over the anvil window. This movement causes material drawn into the window to be cut by the cutting tool and the cut material is drawn into the inner shaft and is evacuated by vacuum towards the proximal end of the outer shaft.

In certain aspects, the cutting device is navigatable within a subject such as within the confines of the invertebral disc or nucleus. The navigation may be aided by providing a desired degree of curvature in a distal portion of the device. The curvature can be provided by (1) a curved distal end portion on the outer shaft; (2) a curved distal end portion on the inner shaft; (3) a curved distal end portion on a wire inserted into the outer shaft; or (4) all or any of the ways 1-3 or other components contemplated by those skilled in the art on reading this disclosure.

In other aspects of the invention the device is moved or navigated through a desired space by the use of control wires which can be tensioned, loosened, or compressed to curve the distal portion of the device in one direction or another. The control wires can be used by themselves or in combination with any or all of 1-4 above.

In yet another aspect of the invention there is provided a kit comprised of a plurality of wires which have a curved distal end portion wherein each wire is curved in a different amount relative to other wires. The user can choose one wire and determine the amount of curvature obtained. Thereafter a different wire with more or less curvature can be used. The device can be sold as a kit with a plurality of curved wires and the plurality of curved wires can be sold together as a separate kit. At least one wire may be inserted through the lumen of the flexible shaft of the device which then changes the curvature of the flexible shaft, thereby repositioning the cutting window in the anvil within the disc.

In other aspects, the subject devices are used in methods of performing a selective percutaneous discectomy.

An aspect of the invention is to provide a flexible surgical cutting device which is able to navigate through the nucleus pulposus.

Another aspect of the invention is to provide a flexible surgical cutting device which is capable of navigating through the nucleus pulposus to a target site within the nucleus.

Another aspect of the invention is to provide a flexible surgical cutting device which is capable of directly accessing a site of herniation without damaging the intervertebral disc at the herniation site.

Another aspect of the invention is to provide a flexible surgical cutting device which includes a cutting mechanism to selectively remove nucleus pulposus material from a specific target site.

Another aspect of the invention is to provide a flexible surgical cutting device which includes a cutting mechanism to selectively remove nucleus pulposus material from within the nucleus.

Another aspect of the invention is to provide a flexible surgical cutting device which is capable of excising nucleus pulposus material directly at the site of herniation.

Another aspect of the invention is to provide a flexible surgical cutting device which is able to navigate from a posterolateral extrapedicular entry point through the confines of the nucleus to a herniation site within a fissure located at the posterior wall of the annulus.

Another aspect of the invention is to provide a flexible surgical device which is configured to curve upon entry into the nucleus.

Another aspect of the invention is to provide a flexible surgical device comprising a curved distal portion wherein the amount of the curvature is adjustable while it is positioned within the invertebral disc.

Another aspect of the invention is to provide a flexible cutting device comprising components that have elastic or shape memory characteristics.

Another aspect of the invention is to provide methods of navigating a cutting device within the intervertebral disc to a specific target site.

Another aspect of the invention is to provide methods of using a control wire to steer a cutting device within the intervertebral disc to a specific target site.

Another aspect of the invention is to provide methods of navigating a cutting device within the intervertebral disc to a specific target site by adjusting the curve of the shaft.

Another aspect of the invention is to provide methods of navigating a cutting device within the nucleus pulposus to a specific target site by adjusting the depth of a cannula.

Another aspect of the invention is to provide methods of treating a herniated disc by navigating a cutting device within the confines of the nucleus to a specific target site within the intervertebral space.

Another aspect of the invention is to provide methods of treating a herniated disc by navigating a cutting device within the confines of the nucleus to a herniation site within a fissure.

Another aspect of the invention is to provide a method for treating a herniated disc in which the cutting device enters the nucleus from the side contralateral to the herniation and directly approaches the herniation site from within the nucleus.

Another aspect of the invention is to provide a method of navigating a cutting device within the intervertebral space by changing the position of the cutting mechanism of the device by inserting at least one stylus (which may be chosen from a set, each with different curvatures) into the lumen of the shaft to change the curvature of the shaft.

These and other aspects of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 2A open, 2B closed, 2C open, 2D closed, 2E open, 2F closed provide a cross-section view of the cutting device in an open and closed window position in accordance with an embodiment of the invention.

DETAILED DESCRIPTION OF THE INVENTION

Before the present devices and method of treatment are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a lumen" includes a plurality of such lumens and reference to "the control wire" includes reference to one or more control wires thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Flexible Navigatable Cutting Device

Figure 9:
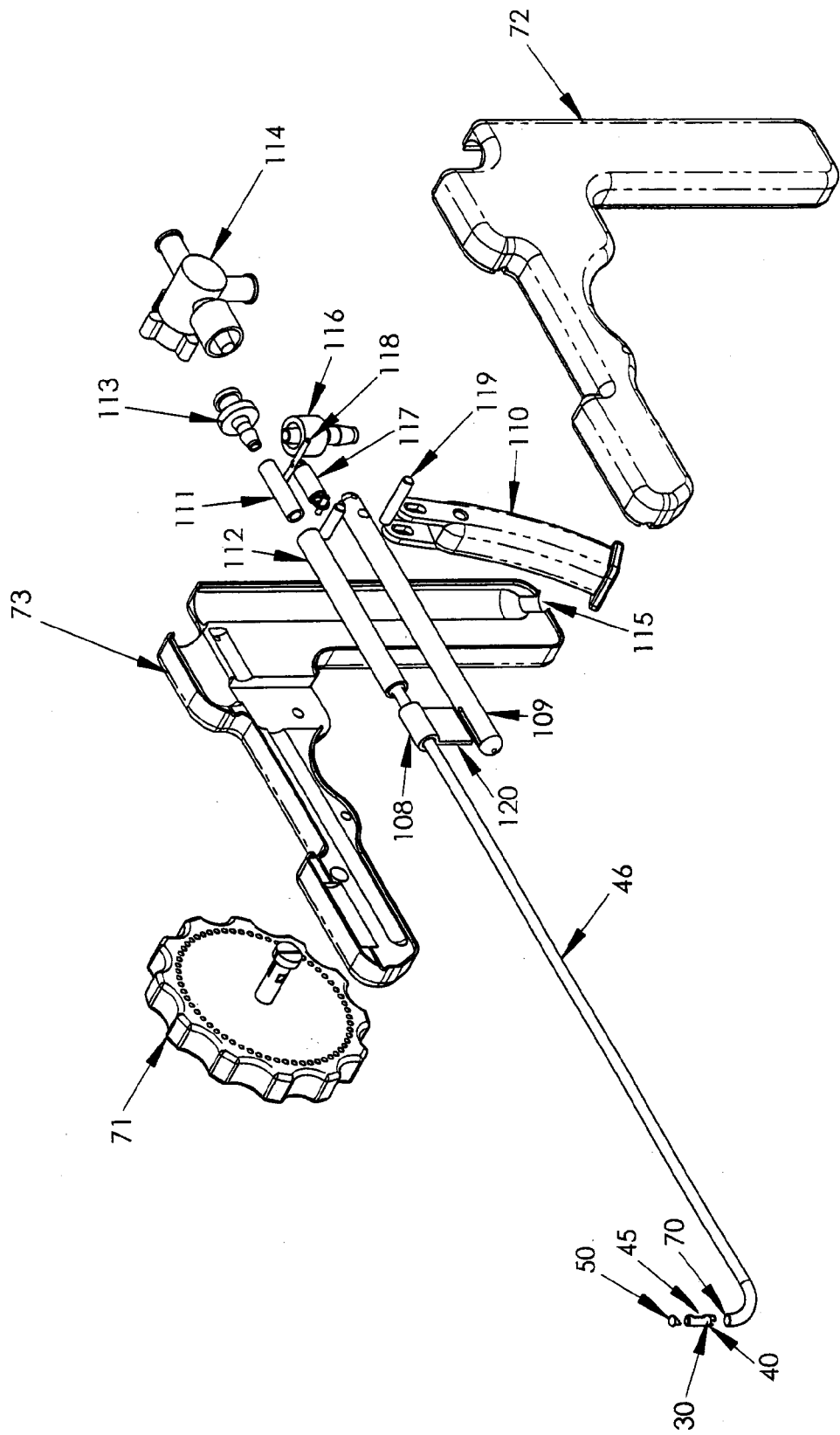
FIG. 9 is a schematic exploded view of the device of FIG. 10.

The distal portion of the device 10 as shown in FIGS. 2A-2F can be configured in a number of different embodiment's 2A-2F. Those embodiments shown here should not be considered as a limitation on the scope of the invention. However, there are features and characteristics of the invention which may be shared by embodiments of the invention. One of these features includes the ability to insert the device contralateral or anterolateral to a point of herniation as shown within FIG. 7. In accordance with another feature the distal end portion 10 of the device as shown in FIG. 2 can be bent as shown in FIG. 9. The bending can be accomplished using a number of different embodiments. For example, the outer shaft shown in FIGS. 2A-2F can have a preformed curve. Alternatively, the inner shaft 101 as best shown in FIGS. 2E and 2F can have a curved configuration at its distal end portion. Alternatively, a stylus or bent wire 103 as shown in FIG. 2E can be inserted within the outer shaft 100 or inner shaft 101 to create a desired degree of curvature. The device may be sold as a kit which includes a plurality of bent wires or styli 103 wherein each stylus has a different degree of bend relative to any other stylus in the kit. When the distal portion o the device 10 is in place in the patient it can be navigated by including a first stylus to obtain a desired degree of bending or curvature. The shape of the curvature in the stylus may represent a three dimensional curve (i.e. curvature in specific known amounts in each of two different parallel planes) that allows the operator to approach the disk at an angle to the plane of the disk and maneuver the device along the plane of the disk. The stylus can then be moved to the desired location. If this degree of bending or curvature is no longer desired the stylus can be removed to allow straightening or can be removed to insert a different stylus with a different degree of bending. In this manner it is possible to slowly navigate the distal end portion of the device 10 to its desired location.

As shown in FIGS. 2A-2F the window 45 can have a number of different configurations. The window is preferably positioned along side of material related to the herniation which material is to be removed. Once the window is correctly positioned suction is applied and material is drawn into the window and into a hollow area 104. While continuing to hold the material within the window and in the hollow area the distal member 50 also referred to as the safety tip 50 which forms part of the inner shaft is pulled backwards toward the cutting mechanism 30 which includes a blade 105 which goes around the entire circumference of the distal end of the outer shaft 100 as shown in FIG. 2E.

The diameter of the blade 105 at the end of the cutting member 30 is slightly smaller than the outer diameter of the safety tip 50. Accordingly, the safety tip 50 cannot be drawn inside the outer shaft. Thus, the blade 105 will not cut material unless it is drawn into the window 45 and moved backwards against the blade 105. This provides a significant safety advantage when carrying out a delicate operation.

Figures 1A, 1B:
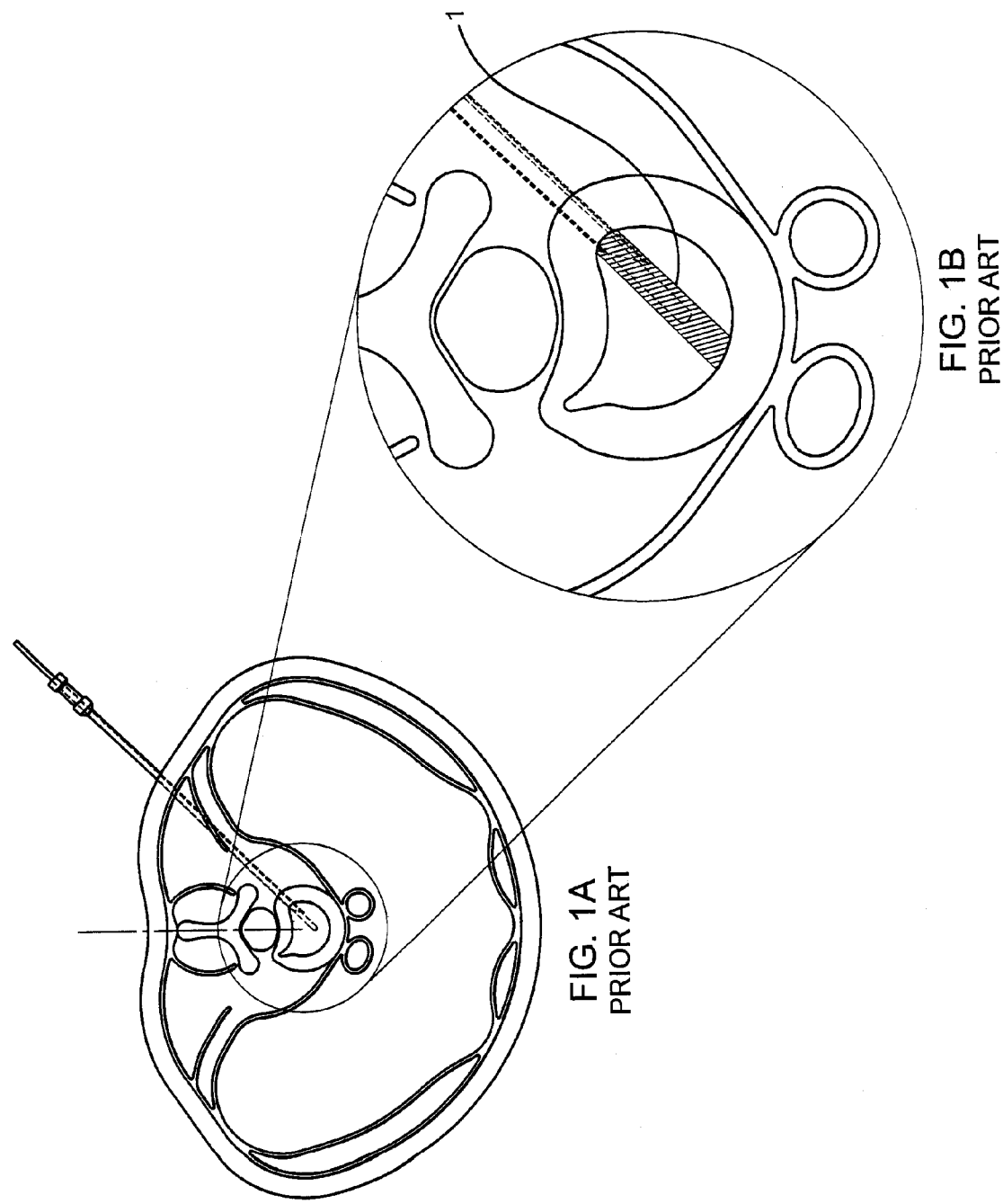
FIG. 1 includes sections 1A and 1B which show an embodiment of a PRIOR Art discectomy device.
Figure 3:
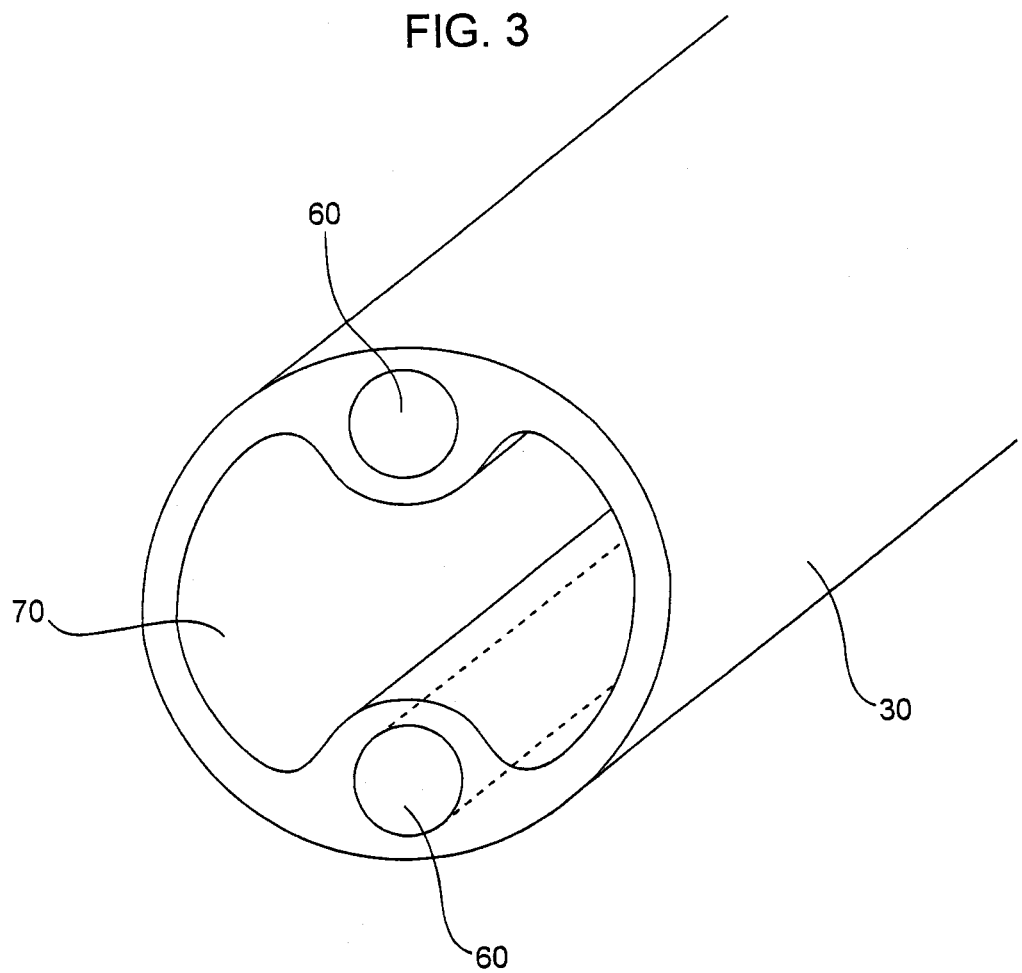
FIG. 3 provides a cross-section view of a portion of the device in accordance with an embodiment of the invention.

Those skilled in the art will understand that there are other components which can be used to navigate or control the position of the cutting device 10. For example, within FIG. 3 are shown control wire 60. By pulling on one control wire and relaxing the other it is possible to obtain a degree of bending of the distal end portion of the device. This bending can be relaxed, readministered or turned in the opposition direction as desired. As shown in FIG. 2E the distal end member of safety tip 50 prevents the cutting blade 105 shown in FIG. 2E from cutting unwanted tissue as the device is positioned in the desired location. Because the flexible shaft 20 can bend it is possible to position the anvil 40 which includes the window 45 in any desired location.

As shown in FIG. 3 the hollow opening 70 may run the entire length of the device. The opening 70 may be used to provide a vacuum which sucks material into the window 45. Alternatively the hollow opening 70 may be used to extrude material including water, saline, or a pharmaceutical formulation comprising an excipient and a pharmaceutically active drug. The formulation may also be comprised of an excipient and a desired marker such as any type of dye as described herein for use in determining the position of the device relative to bone tissue and a desired target site. The liquid may be sterile water or saline extruded at a rate and manner to loosen material at a herniation site or where needed and thereafter evacuated through a lumen.

Figure 8:
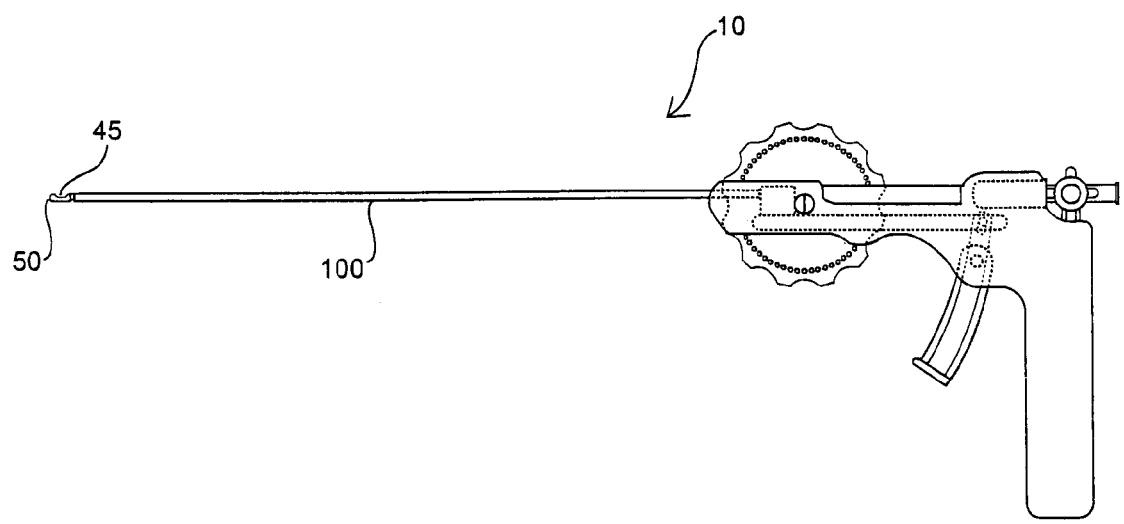
FIG. 8 is a schematic view of the entire device of the invention in cross-section.

An overall schematic view of the entire device 10 can be seen in FIG. 8. The elongated outer shaft 100 is shown with the distal end having the window 45 and safety tip 50 positioned thereon. The proximal end of the device comprises the control mechanism as shown in FIG. 8.

The present invention is drawn to a flexible surgical cutting device which is navigatable within the confines of the nucleus for selective percutaneous discectomy. As such, the subject devices are capable of navigating through the nucleus pulposus to directly access a specific site within the nucleus without causing any damage to the intervertebral disc. The subject devices include a cutting mechanism to selectively remove nucleus pulposus material from a specific target site. In certain aspects, the target site is a specific site within the nucleus. In other aspects, the target site is the specific site of injury, i.e., the herniation within the fissure. In some embodiments, the subject devices directly excise nucleus pulposus material at the site of herniation. In certain aspects, the subject devices are able to navigate from a posterolateral extrapedicular (or anterior or anterolateral) entry point through the confines of the nucleus to a herniation site located within a fissure at the posterior wall of the annulus. In a particular embodiment, the subject devices are able to enter the nucleus from the side contralateral or anterolateral to the herniation and directly approach the herniation site from within the nucleus.

In the embodiment illustrated in FIG. 2E, the cutting device (10) includes a shaft assembly which comprises an outer flexible shaft (100) having a cutting mechanism (30) and an inner shaft comprising an anvil (40). In certain embodiments, the internal shaft will have a cutting window that comprises a distal window (45). The outer shaft and the inner shaft are concentric to one another such that the inner shaft is positioned within the outer shaft. In some aspects, the cutting device further comprises a distal member (50) that is larger in diameter then the cutting mechanism (30). Therefore, when the cutting mechanism is advanced (60) it cannot be advanced beyond the distal member (50). In certain embodiments, the distal member includes a beveled distal tip which aids in the navigation through the thick gelatinous nucleus pulposus. In other embodiments, the distal member has a blunt distal tip which will deflect away from neural structures or blood vessels and not pierce or damage intervertebral structures. Additionally, the blunt distal tip prevents the subject devices from penetrating through the fissure or tearing through the annulus.

The shaft assembly of the cutting device may be straight, curved, rigid, flexible, steerable or any combinations thereof as long as the shaft assembly has adequate column strength to navigate through the nucleus pulposus without collapsing. In some embodiments, the shaft assembly has a diameter ranging from about 0.060 inches to about 0.200 inches, where in certain embodiments, the shaft ranges from about 0.080 inches to about 0.180 inches while in other embodiments, the shaft ranges from about 0.100 inches to about 0.160 inches. The length of the shaft may range from about 4.00 inches to about 15.00 inches, where in certain embodiments, the length ranges from 6.00 inches to about 13.00 inches while in other embodiments, the length ranges from 8.00 inches to about 11.00 inches.

In certain aspects, the shaft assembly of the present invention is made from a material that provides elastic or shape memory characteristics. Examples of materials that have elastic or shape memory characteristics include, but are not limited to, Pebax, Nylon, Nitinol, PVC, Stainless Steel wire and Nitinol wire. By "shape memory characteristics" is meant a material that may be deformed by the application of a force and fixed into a temporary shape but is capable of recovering its' original, permanent shape when subjected to an increase in temperature. In one embodiment, the shaft may be a braided structure such that the flexibility of the shaft may be adjusted by varying the configuration of the braiding pattern or the location of the braid. Further, the flexibility and mechanical properties of the shaft may be modified by wrapping a wire around the shaft in a coiled fashion to reinforce or modify the flexibility of the shaft. The properties and spacing of the wire may be modified to achieve a variety of parameters.

Aspects of the invention include curving the distal portion of the subject cutting device such that upon entry into the nucleus, the subject device is configured to curve to the site of herniation from within the confines of the nucleus. As such, the subject devices will be shaped in a curved fashion but remain flexible enough to pass through a straight cannula. The radius of the curve is preformed so the device is navigable through the confines of the nucleus to a specific target site. In certain embodiments, the curve is "j shaped" while in other embodiments, the curve is "c shaped." In certain embodiments, the curvature is a three dimensional curve to enable access to the disk at an angle to the plane of the disk. The device may then follow the plane of the disk as it exits the cannula. In some embodiments, the subject devices are curved in such a manner that the target site is a specific site within the nucleus. In other embodiments, the specific target site is the site of herniation. In these embodiments, the subject devices are curved to directly advance to the site of herniation and excise the injured nucleus pulposus and fragmented annulus material. In certain aspects, upon entry from a posterolateral extrapedicular entry point, the subject devices are curved to directly enter a herniation site located within a fissure at the posterior wall of the annulus. In a particular embodiment, the subject devices enter the nucleus from the side contralateral or anterolateral to the herniation and are curved to directly approach the herniation site through the nucleus.

In certain embodiments, the distal window (45) may be bisected by an internal rib (46) as shown in 2E. The outer cutting mechanism is advanced by sliding the outer shaft over the internal shaft. When the outer shaft is not advanced, the cutting window is considered to be "open" as illustrated in the embodiments of FIGS. 2A, 2C and 2E. When the outer shaft is advanced towards the distal end of the inner shaft, the cutting window is considered to be "closed" as in FIGS. 2B, 2D and 2F. Aspects of the invention include navigating the flexible cutting devices with a "closed" cutting window through the confines of the nucleus to a specific target site. Once positioned at the specific target site, the outer shaft is retracted away from the distal end to open the cutting window directly at the site of injury. In certain aspects, the cutting window will be positioned directly at the site of herniation. In a specific embodiment, the cutting window will be positioned directly at a herniation site within a fissure located at the posterior wall of the annulus.

The cutting window of the subject device may be any suitable shape such as, but not limited to, rectangular, circular, oval, square, or triangular. The length of the cutting window may range from about 3 mm to about 8 mm, where in certain embodiments, the length ranges from about 4 mm to about 7 mm while in other embodiments, the length ranges from about 5 mm to about 6 mm. The cutting window opening may describe an arc with a range of 60 degrees to 300 degrees, where in certain embodiments the arc ranges from 120 degrees to about 240 degrees and in other embodiments, the arc ranges from 160 degrees to about 200 degrees.

In certain aspects, the cutting mechanism is positioned at the distal end of the outer shaft and is capable of sliding over the inner shaft to cut material positioned within the distal window of the cutting window. In some embodiments, the actual circumference of the distal end of the outer shaft includes the actual cutting mechanism itself. Aspects of this embodiment include cutting blades that are "o" shaped and positioned at the tip of the distal portion of the outer shaft. In certain aspects, the subject devices may include a cutter in which the sharpened edges are angled. In some embodiments, the cutting mechanism is configured to excise tissue by rotating. As such, the outer shaft may be advanced and rotated to excise the tissue positioned within the open window of the cutting window. In some embodiments, the cutting mechanism excises nucleus pulposus at a site directly within the nucleus. In other embodiments, the cutting mechanism excises nucleus pulposus directly at the site of herniation within the fissure. In a specific embodiment, the cutting mechanism excises nucleus pulposus from within the confines of the nucleus at a herniation site located within a fissure at the posterior wall of the annulus.

As discussed above, the anvil includes a cutting window that is open or closed by advancing and retracting the outer shaft over the inner shaft. The anvil of the subject devices may be made from rigid or flexible materials such as but not limited to Pebax, Nylon, Nitinol, PVC, Stainless Steel wire, Nitinol wire or from a plastic molded or extruded material. In a specific embodiment, the anvil includes an extrusion made from a material that has shape memory or elastic characteristics which may be attached to a rigid anvil tip, thereby allowing the anvil to be rigid or flexible. In another embodiment, the extrusion may form the anvil itself. In certain embodiments, the cutting device does not include an anvil. In this particular embodiment, the cutting window is directly located at the distal portion of the inner shaft.

In some embodiments, the distal end of the cutting device may be made of a radiopaque material or include one or more radiopaque markers at its distal end or throughout spaced locations. For example, suitable materials may include, but are not limited to, barium sulfate, bismuth trioxide, iodine, iodide, titanium oxide, zirconium oxide, metals such as gold, platinum, silver, tantalum, niobium, stainless steel, and combinations thereof.

In certain aspects, the shaft assembly may include a plurality of lumens. In a specific embodiment, the additional lumen includes a control wire that is tensioned or compressed to provide steerage control of the device within the confines of the nucleus. In some embodiments, the cutting devices include more than one control wire. In certain aspects, the control wires may be made of a shaped memory or elastic material to further guide the subject device to a specific target site. Examples of materials that have elastic or shape memory characteristics include, but are not limited to, Pebax, Nylon, Nitinol, PVC, Stainless Steel wire, Nitinol wire and plastic. In certain aspects, the control wires may be flat, round or tapered. As illustrated in the embodiment in FIG. 3 and FIG. 2E, the anvil (40) of the inner shaft may have multiple lumens where at least one of the lumens has at least one control wire (60) running through it. In some embodiments, the control wires are attached to the proximal end of the anvil.

In certain embodiments, the distal portion of the control wire may include a spring coil to adjust the flexibility. A forming ribbon may be incorporated in the distal portion of the control wire to support the spring coil. The spring coil may be fully coated with Teflon or other biocompatible materials. The distal portion of the control wire may be tapered to a smaller diameter toward the distal end. The control wire is also preferably radiopaque so as to be visible under fluoroscopy.

The actual dimensions of the control wire will vary with the stiffness and tensile strength of the material used to form the control wire. The control wire may also have various other shapes other than tapered or a flattened ribbon such as triangular, oval, wedge or rectangular in cross-sectional shape. In some embodiments, the control wire preferably has a total length greater than or at least equal to the length of the shaft assembly.

In certain embodiments, a deflectable stylus consisting of shaped memory or elastic material that is encapsulated by a straight, rigid sheath may be inserted into the shaft of the device through the proximal end of the device. Once the stylus (wire with a distal end portion with a known curvature) and sheath are in place, the sheath is retracted to allow the stylus to return to its' curved shape. The stylus may have a radius of curvature that is greater than or less than the preformed curvature of the shaft. Therefore, the presence of the stylus within the shaft of the device causes the radius of curvature of the shaft to increase or decrease depending on the corresponding curvature of the stylus. The sheath is typically but not necessarily withdrawn from the stylus while the shaft is still constrained by the cannula. The shaft is then advanced distally out of the cannula and into position at the site of herniation. The stylus is then withdrawn from the distal end of the shaft and into the sheath wherein both components are withdrawn from the shaft of the device to enable the debulking process to commence.

In certain embodiments, a deflectable stylus consisting of shaped memory or elastic material may be inserted into the shaft of the device to establish a radius of curvature of the shaft. Several styli with a variety of curvatures may be supplied to allow the operator to choose the radius of curvature desired for a particular treatment modality allowing the window to be placed along side of material to be removed such as along side of the herniation. The stylus may be inserted into the shaft and the shaft may then be advanced to the cutting site and the debulking process may commence with the stylus still in position within or adjacent to the shaft.

In certain embodiments, several styli may be used to enable the operator to maneuver the shaft of the device to a position within the disc that requires the shaft of the device to follow a complex, three dimensional curvature, such as is typically required to access the L5-S1 intervertebral disc. In this embodiment, each stylus has a slightly different curvature that when used in progression, enables the shaft to be advanced to a position that cannot be obtained by a single stylus described which has a single curvature.

The subject devices generally include a handpiece which is ergonomically molded and contoured to fit comfortably within the palm of a hand. In certain aspects, the handpiece is composed of a durable and rigid material, such as medical grade polymer of desired structural integrity. In some embodiments, the handpiece includes a molded polymeric housing which encloses a small motor and a power supply. In certain embodiments, the handpiece may include a rotatable wheel member which is directly connected to the control wires. By rotating the knob member, the user is able to adjust the control wires to navigate through the nucleus pulposus to a specific target site. In some embodiments, the rotating wheel member is able to adjust the curve of the control wire, which in turn, controls the radius of curvature of the subject cutting device shafts. In these embodiments, the control wires are attached to the wheel member so that when rotated in a first direction, tension is applied to the control wire, thereby causing the radius of shaft curvature to decrease. By rotating the wheel member in a second direction, the tension is reduced, thereby causing the shaft radius of curvature to increase at its distal end. By adjusting the rotating wheel, the curvature of the shaft may be adjusted in micrometer intervals, which in turn adjusts the curvature of the subject cutting devices. In other embodiments, the rotatable wheel may be replaced with a lever or sliding shuttle mechanism attached to the control wire(s) to accomplish the desired effect.

As illustrated in FIG. 3, the anvil (30) of the inner shaft has multiple lumens for control wires (60) but may have additional lumens for treatment modalities. As such, the subject devices allow additional treatment methods to be performed directly at the site of herniation. For example, additional treatments include but are not limited to aspirating material, providing make up air that allows a pressure differential on the excised tissue and causes it to evacuate from the operative site, delivering medicaments, delivering injection dye or providing a liquid jet. Additionally, the lumens within the shaft may be used to allow passage of a visualization device such as a fiber optic camera. Alternatively, the fiber optic system may be integrated into the design of the shaft.

In certain embodiments, the additional lumen may be employed to provide a vacuum source. In this embodiment, the vacuum source is used to evacuate the tissue excised within the cutting window. In some aspects, the cutting device includes a lavage channel. As such, the instant invention is configured to create an aspiration force for withdrawing material excised by the subject cutting devices.

In some embodiments, the cutting device is connectable to an external aspiration source, such as a vacuum. While in another embodiment, the aspiration source is self-contained within the device, thereby not requiring an external aspiration source. For example, the subject devices may include a $CO_2$ cartridge or a vacuum reservoir. The vacuum source provides the suction force for withdrawing material during the cutting process or after the nuclear material has been cut by the subject devices. For example, in some embodiments a $CO^2$ cartridge is used to create a vacuum via a venturi or by actuating a piston that creates suction within the shaft of the cutting device.

In some aspects, the vacuum source may also provide a suction which positions the tissue within the cutting window prior to excising the tissue. In certain aspects, the excised material is drawn from the nucleus into the window of the inner shaft of the subject devices, cut by the cutting element, and then drawn outside of the patient's body. In a specific embodiment, the vacuum source is connected to or included within the housing of the handpiece. In certain aspects, the handpiece of the cutting device may additionally include a valve positioned to disconnect the shaft of the device from the vacuum source and allow additional devices such as catheters and styli to be advanced through the lumen of the subject cutting devices. The valve directs the opening to the inner shaft to the vacuum source or to an opening in the proximal end of the instrument.

The subject devices may further include a tissue collection chamber which is structured to collect and contain the nuclear material excised by the subject cutting devices. In certain embodiments, the collection chamber is made of a transparent material, thereby allowing direct visualization of the excised tissue. In other aspects, the collection chamber may facilitate the quantification and/or other analysis of the material removed from the intervertebral disc. In a particular embodiment, the collection chamber is directly connected to or part of the housing of the handpiece of the subject cutting devices. In another embodiment, the collection chamber may be located along the vacuum tubing between the handle and the vacuum source.

In another embodiment, the anvil may include an additional lumen for injecting radiopaque dye into the operative site for visualization purposes. For example, dilute barium soleplate solution may be injected through the lumen into the nucleus and the patient scanned using radiographic techniques. Additional suitable materials that provide radio-opacity are well known in the art such as bismuth trioxide, iodine, iodide, titanium oxide, zirconium oxide, metals such as gold, platinum, silver, tantalum, niobium, stainless steel, and combinations thereof.

In certain embodiments, the additional lumen is employed to deliver a medicament within the disc. For example, the lumen may deliver a pharmaceutical agent, chemonucleolytic enzymes, hydrogel substances, osteoinductive substances, chondrocyte-inductive substances, sealants, collagen, fibrinogen, thrombin and combinations thereof.

In some embodiments, the additional lumen is a pressure lumen which delivers a liquid jet for cutting and removing nucleus pulposus material. The pressure lumen is configured to have sufficient burst strength to enable it to conduct a high pressure liquid through a nozzle, thereby forming a liquid jet. The burst strength should be selected to meet and preferably exceed the highest contemplated pressure of the liquid supplied for use in the discectomy. The liquid utilized for forming the liquid jet may be any fluid that can be maintained in a liquid state at the pressures and temperatures contemplated for performing the discectomy. The liquid should be physiologically compatible, for example, typical liquids include but are not limited to saline solution or sterile water. In certain aspects, the pressure fluid is adjustable between low pressure and high pressure. In some embodiments, the subject devices include a deflector which prevents the liquid jet from being misdirected during use. Aspects of this embodiment include delivering a high pressure fluid through the lumen to cut, remove or to loosen adherent fragments of nucleus pulposus material to facilitate excising and removal of material by suction.

In certain embodiments, the surgical devices are disposable. By "disposable" is meant that the device may be "disposed of" or "thrown away" after use in a single patient. The device may be sterilized, placed in a sterile container, removed from the container immediately prior to use, used and thereafter discarded.

It will be apparent to those of skill in the art that the subject cutting devices may be delivered to the intervertebral disc using techniques and apparatuses readily well known in the art. Typically, the subject devices are advanced through the lumen of an introducer. The introducer, in its simplest form, can be comprised of a hollow needle-like device (optionally fitted with an internal removable obturator or trocar to prevent clogging during initial insertion) or a combination of a simple exterior cannula that fits around a trocar. The result is essentially the same: placement of a hollow tube (the needle or exterior cannula after removal of the obturator or trocar, respectively) through skin and tissue to provide access into the annulus fibrosis. The hollow introducer acts as a guide for introducing instrumentation. More complex variations exist in percutaneous instruments designed for other parts of the body and can be applied to design of instruments intended for disc operations. Examples of such obturators are well known in the art. A particularly preferred introducer is a 17- or 18-gauge, thin-wall needle with a matched obturator, which after insertion is replaced with a probe of the present invention In certain aspects, guide wires are employed as a placeholder to access the intervertebral disc. The guide wire may be manufactured from a high strength alloy containing cobalt, nickel, chromium or to a composite product having a portion formed of an alloy and a superelastic alloy such as Nitinol.

In some embodiments, a cannula is employed to introduce the cutting devices of the present invention into the intervertebral disc. The cannula generally comprises a tubular structure which serves as a conduit extending between the exterior of the body and the intervertebral disc. Essentially, the subject cutting devices advance through the cannula to the intervertebral disc. The interior of the cannula may also be coated to improve the ability of the shaft to transfer tissue through the shaft. Such coatings include but are not limited to parylene, silicone, polyimide and the like. The inner lining and coating also provides for smooth gliding over the guide wire to prevent kinking or snagging of the cannula. In some embodiments, the subject devices advance through the distal tip of the cannula. In other embodiments, the cannula includes an orifice. Aspects of this embodiment include advancing the subject devices through the cannula and out via the orifice. By adjusting the position of the orifice, the entry point of the subject devices within the nucleus may additionally be controlled.

In certain embodiments, the subject devices may further include a dilator sheath which is configured to slide or pass over the guide wire for introducing the cannula onto the guide wire. The sheath may be made of a variety of materials including but not limited to polyester, rayon, polyimide, polyurethane, polyethylene, polyamide and silicone. The dilator sheath supports the cannula and guide wire when the cannula is advanced through the body percutaneously and also protects the cannula from any collateral damage that may be associated with inserting the cannula over the guide wire. The dilator sheath also provides a conduit for the cannula into the nucleus when the cannula encounters resistance which could damage the treatment modalities associated with the cannula and the subject devices.

Methods of Navigating a Cutting Device Within the Nucleus Pulposus

Once the flexible cutting devices are introduced into the nucleus, the subject devices are able to navigate and maneuver through the gelatinous material of the nucleus pulposus. Aspects of the invention include curving the distal portion of the subject devices such that upon entry into the nucleus, the subject device is configured to curve away from the distal end of the cannula at an angle ranging from 15 degrees to 90 degrees. In some embodiments, the angle ranges from 30 degrees to 75 degrees while in other embodiments, the angle ranges from 45 degrees to 60 degrees. In certain embodiments, the cutting device is configured to curve away from the distal end of the cannula towards the posterior wall of the annulus. In certain aspects, the preformed curve enables the flexible cutting devices to directly access the nucleus pulposus within the disc plane regardless of which disc is specifically injured. The anatomical location of certain discs requires that the cannula must approach and enter the disc at an angle to the disc rather than in the same plane as the disc. Therefore, a particular embodiment is configured to compensate for this angle by advancing beyond the distal end of the cannula in a curved plane that is at an angle to the cannula.

The subject cutting devices may be steered in a particular direction by adjusting the depth of the cannula within the nucleus. By advancing the cannula into the nucleus, the subject devices are navigated to an area which is further away from the cannula site of entry. In certain embodiments, the subject devices employ rails that allow the cannula depth to be adjusted by sliding the cannula backwards and forwards. By drawing back the cannula, the radius of curvature of the shaft may be increased and the subject devices are able to access an area of the nucleus which is further away from the cannula site of entry. Conversely, if the cannula is inserted more deeply into the disk after the distal end of the device is already in the nucleus, the radius of curvature of the device may be decreased and the subject devices are able to access an area of the nucleus which is closer to the cannula site of entry. As such, the subject cutting devices may be steered through the nucleus pulposus and navigated to a specific target site by adjusting the depth of the cannula within the nucleus pulposus and preforming the device to a specific curve.

The subject cutting devices may be steered by advancing the shaft of the cutting device from the distal tip of the cannula and subsequently adjusting the depth of the cannula within the disc. By increasing the depth of the cannula, the radius of curvature of the shaft is decreased and by decreasing the depth of the cannula, the radius of curvature of the shaft is increased. As a result, the operator may redirect the shaft of the device while advancing it.

Figure 4:
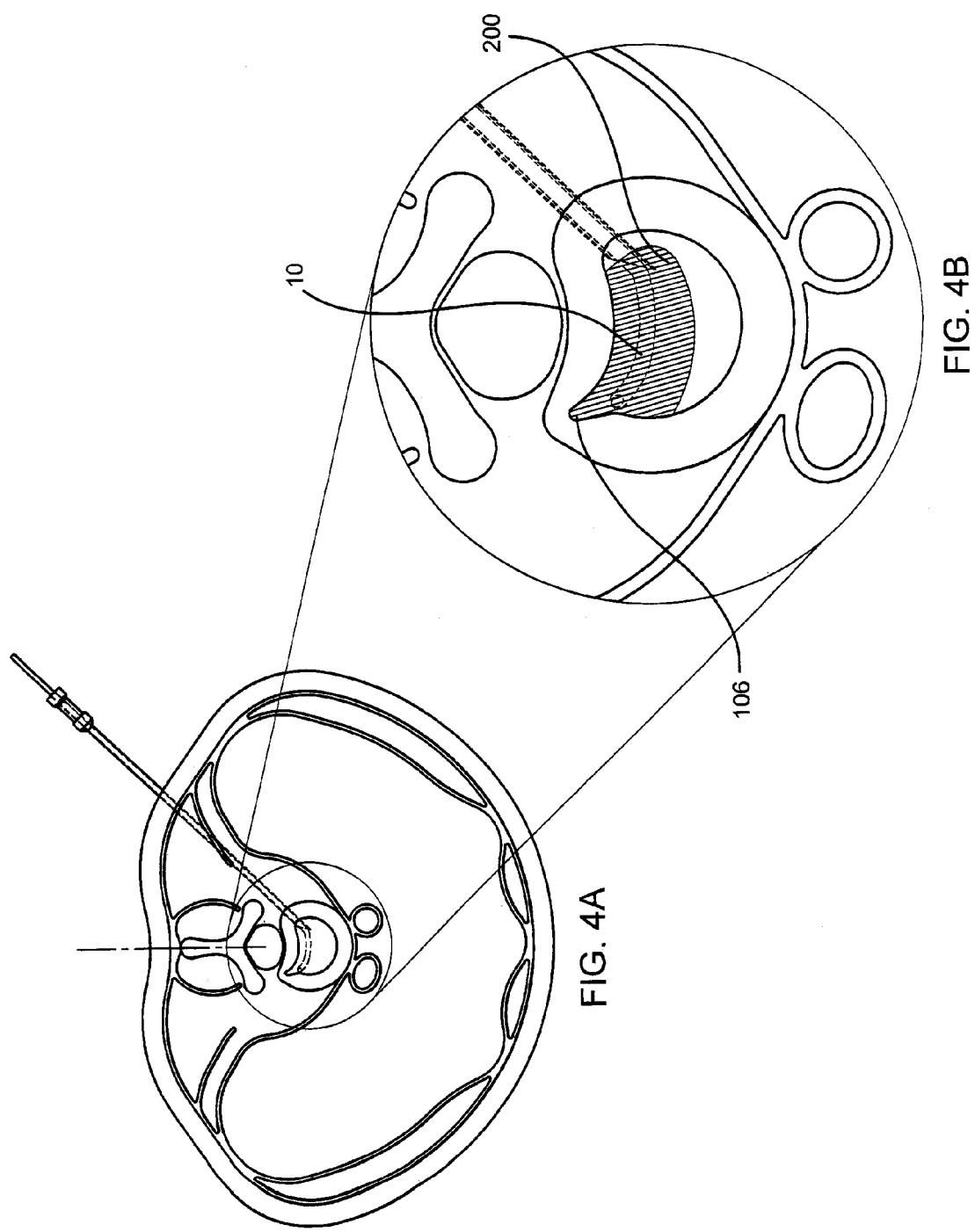
FIGS. 4A, 4B, 5A, 5B, 6A and 6B illustrate the various target areas within the nucleus in which the subject devices are able to access.

One aspect of the invention provides a method of treating a herniated disc by performing a selective percutaneous discectomy. The patient is first diagnosed as having a herniated disc. The patient is then subjected to imaging such as MRI imaging in order to determine the location of the herniation. At this point markers which can be viewed on X-ray or other imaging devices may be placed on the surface of and/or within the patient to provide for assistance in navigation. In a manner as described above an introducer is placed into the patient at a point contralateral or anterolateral to the location of the herniation as is shown in FIG. 4A. One or more guidewires are slid through the introducer into the intravertrabal disc. A dilator sheath is advanced over the guidewire and a cannula is slid over the dilator sheath. The disc annulus generally pierced by a mechanism referred to as a trocar. The cutting device of the invention is advanced through the cannula into the nucleus of the intravertebral disc as shown in FIGS. 4A and 4B. In FIG. 4B the portion 200 which is shaded is the posterior portion of the nucleus.

The device 10 of the invention as shown in FIG. 4B is navigated to the point of herniation 106. At this point a vacuum may be applied and material of the herniation 106 may be drawn into the window 45 as shown in FIGS. 2E and 2F. Once the material is drawn into the window the window portion is moved in a direction towards the blade 105 shown in FIG. 2E and cut away. Thereafter the cutaway material can be sucked through a hollow portion of the device and removed from the patient.

Figure 5:
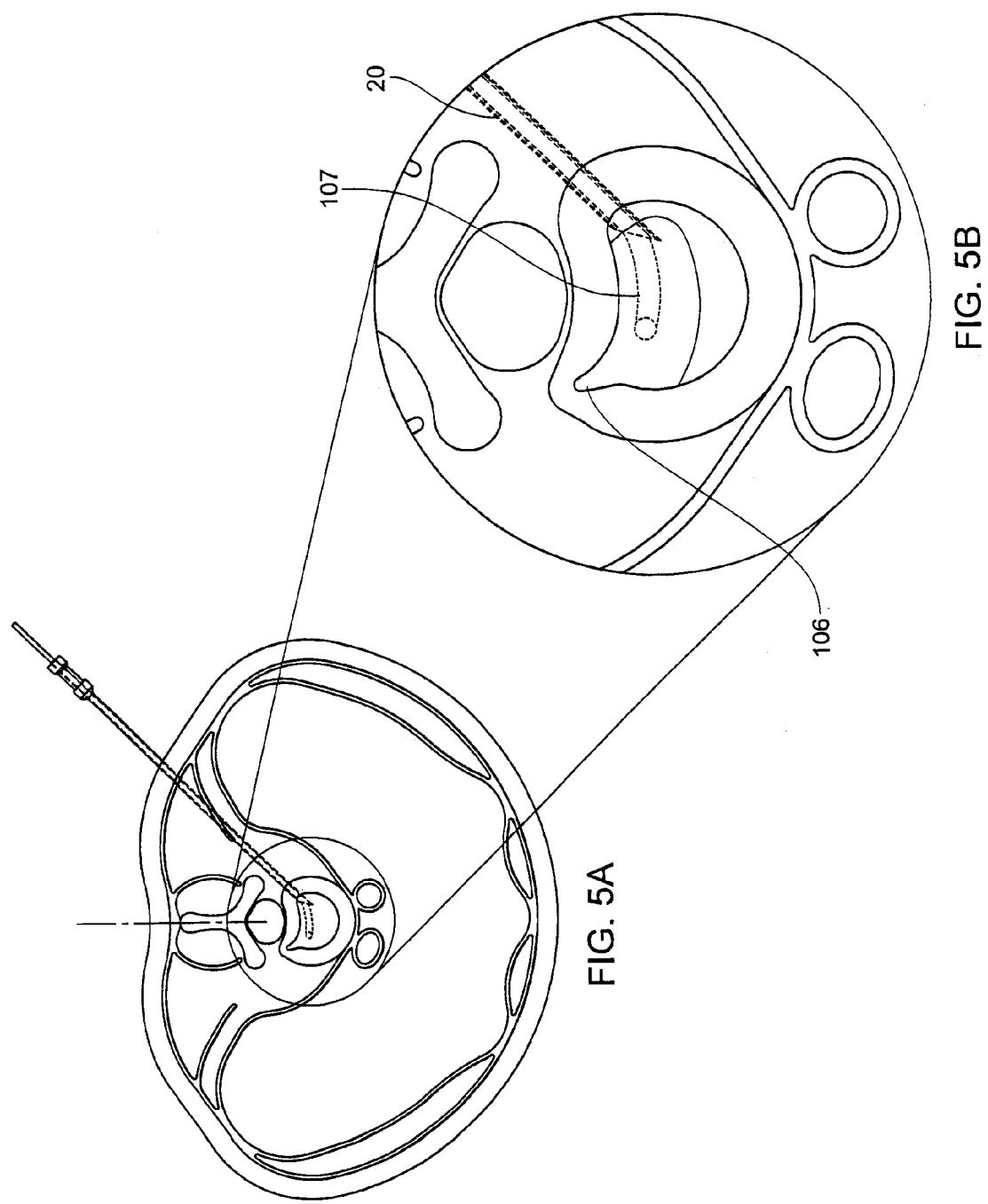

As shown in FIGS. 5A and 5B the flexible shaft 20 is generally inserted contralateral to the herniation 106. The distal portion 107 is curved at an angle which is nearly 90° relative to the shaft 20. At this point a stylus or curved wire 103 is shown in FIG. 2A could be inserted to curve the distal portion 107 further and along with forward movement could place the distal end 50 in close proximity to the target site of herniation 106. The device can be rotated or turned and different types of stylus with different degrees of bend can be used to navigate the window 45 so that it is positioned adjacent to the herniation 106.

Figure 6:
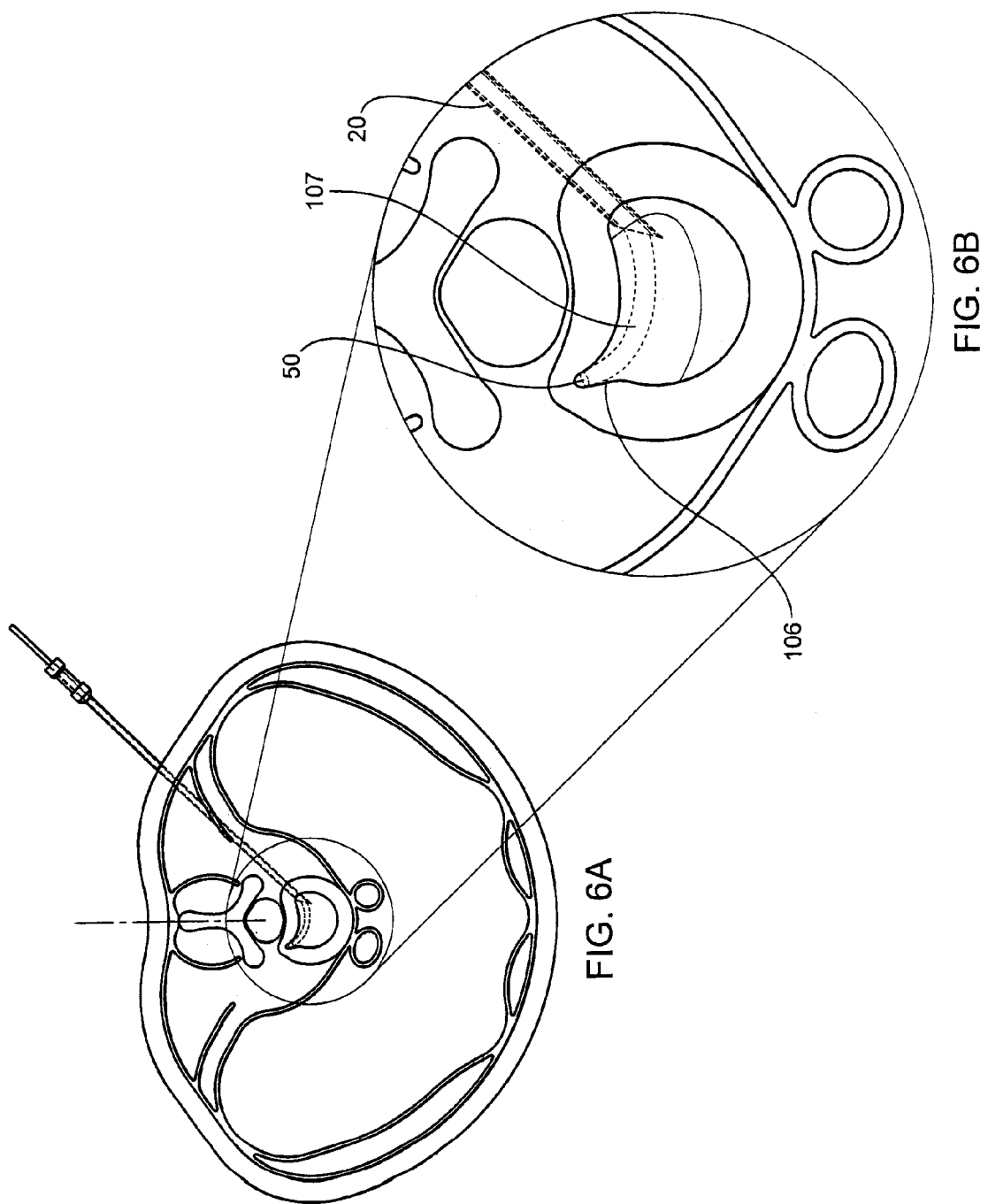

As shown in FIGS. 6A and 6B the distal end 50 of the device is inserted well within the point of herniation 106. The window portion 45 can be seen in FIG. 7. It is at this point that material is drawn into the window 45 and the distal end 50 is retracted into the outer shaft so that the blade 105 cuts the material away so that it can be drawn into the device and out of the patient. One of the features of the invention is that the safety tip 50 is larger in diameter as compared to the circumference of the blade 105. Accordingly, when the safety tip 50 is pulled back against the blade 105 the material inside the window 45 is cut off and the blade is blocked from cutting material which should not be cut.

In some embodiments, the cutting devices employ one or more control wires to steer the anvil to the specific site of herniation from within the confines of the nucleus. In certain embodiments, the cutting device may have one control wire on the outside radius and one on the inside of the radius of the curve around which the anvil or window opening on the inner shaft is to be guided. By compressing the outside control wire and tensioning the inside control wire, the anvil can be directed in a smaller radius than the radius described by the shaped memory or elastic alone. Conversely, by compressing the inside control wire and tensioning the outside control wire, the anvil may be directed in a larger radius than that described by the elastic or shape memory alone. Alternatively, a single control wire may be used on either the inside or outside radius that may be compressed or tensioned to cause the radius of curvature to change.

The cutting device may be navigated and steered through the confines of the nucleus to a specific target site by adjusting at least one or a combination of the specific depth of the cannula, the preformed curved of the device or the control wires. As illustrated in FIGS. 4A and 4B, in certain embodiments, the subject cutting devices may be navigated and steered towards the posterior wall of the annulus. The hatched section (200) of the nucleus depicted in FIG. 4B illustrates the posterior portion of the nucleus. The flexible cutting devices of the present invention are able to access and excise material from target sites within this posterior portion by adjusting at least one or a combination of the specific depth of the cannula, the preformed curved of the device or the control wires.

The target site is a specific site within the nucleus itself as illustrated in FIGS. 5A and 5B. In other aspects, the target site is the specific site of injury, i.e., the herniation site as illustrated in FIGS. 5A and 5B. In certain embodiments, the subject devices navigate from a posterolateral extrapedicular entry point to a herniation site within a fissure located at the posterior wall of the annulus. In a particular embodiment, the subject devices are able to enter the nucleus from the side contralateral to the herniation and directly approach the herniation site from within the nucleus. Therefore, by adjusting at least one or a combination of the specific depth of the cannula, the preformed curved of the device and the control wires, the subject devices are able to excise nucleus pulposus material at a specific target site, such as within the nucleus itself or at a specific herniation site.

The subject devices may not require shaped memory or elastic or steerable characteristics of the cutting device shaft to position the subject devices within the nucleus. Aspects of this embodiment employ at least one guide wire which guides the subject devices to a position within the confines of the nucleus. The guidewire may navigate within an intradiscal section of the intervertebral disc adjacent and/or through an inner wall of an annulus of the disc to a specific site within the nucleus. In other embodiments, at least one guide wire is employed to guide the cannula for accessing the confines of the nucleus. The shaft is capable of being advanced relative to the guide wire such that the shaft follows a path of the guide wire within the intradiscal section of the disc to the selected site within the nucleus.

In a specific embodiment, the subject devices do not include any material having elastic or shape memory characteristics. As such, the control wires in this particular embodiment are compressed or tensioned or combinations thereof to change the direction of the anvil within the confines of the nucleus to access a specific target site. In certain aspects, by compressing or tensioning the control wires or combinations thereof, the cutting devices are able to access and excise material at a target site within the nucleus or a target site specifically at the site of herniation.

The device as shown in an exploded schematic view in FIG. 9 is described below. Those skilled in the art will understand that other embodiments of the invention can be constructed utilizing similar components. Handle embodiments may be changed as features are added and removed from the described embodiment. For example, in its' simplest embodiment, the handle may be designed to actuate the cutting mechanism with no provision for actuating control wires or inserting a stylus.

The Anvil component 40 has vacuum within lumen 70 that pulls tissue into a window 45 to be excised when the cutter 30 advances.

The Safety Tip 50 provides a blunt tip on the end of the Anvil 40 and reduces the likelihood of accidentally penetrating the disk annulus. Additionally, the diameter of the Safety Tip 50 may be larger than the diameter of the Cutter 30 and Anvil 40, thus preventing the cutter 30 from advancing past the Safety Tip 50.

The Control knob 71 used to provide tension or compression on the control wire 60 by rotating the knob 71 clockwise or counter-clockwise. The Control Wire 60 (as shown in FIG. 3) is connected to the Control Knob 71 by inserting it into a slot in the shaft.

The Shaft 46 is comprised of the Cutter Shaft 100 on the outside and the Inner Shaft 101 on the inside (see FIG. 2E). The Inner Shaft 101 has vacuum within a lumen that is used to evacuate excised tissue. The Inner Shaft 101 also has a lumen containing a Control Wire 60 that may also transmit makeup air or saline in the space between the Control Wire 60 and the wall of the lumen (see FIG. 3). The Cutter 30 is attached to the distal extremity of the Outer Shaft 100 and serves to excise tissue that is drawn into the Anvil window 45 when the Outer Shaft 100 is advanced linearly relative to the Inner Shaft 101 (see FIG. 2F).

The function of the Cutter Grasp 108 (see FIG. 9) is to connect the Trigger Shaft 109 to the Outer Shaft 100. The Cutter Grasp 108 has a lumen that encapsulates the Outer Shaft 100 and is bonded to the Outer Shaft 100. The Cutter Grasp 108 has a "key" 120 that is inserted into a slot on the Trigger Shaft 109.

Trigger Shaft 109 transmits linear motion from the Trigger 110 to the Outer Shaft 100 via the Cutter Grasp 108. The Trigger Shaft 109 moves proximally—distally, and is constrained by a channel within the handle halves 72 and 73.

The handle is made of two components, the Handle Left (72) and the Handle Right (73). The function of the Handle Halves is to provide an ergonomically pleasing interface to the operator and house the mechanisms in the handle. The Handle Left 72 and Handle Right 73 components may be made of plastic and either injection molded or machined using clear or opaque materials. The Handle Left 72 and Handle Right 73 may be assembled to one another using mechanical fasteners such as screws, ultrasonic welding, by bonding with solvents or adhesives, or by press fitting together male and female features.

The Adapter Tube 111 connects the Sight Tube 112 to the Luer fitting 113.

The Luer fitting 113 connects the Adapter Tube 111 to the Stop Cock 114.

Sight tube 112 is used as a collection chamber to enable visualization of excised tissue. This visualization allows the user to determine if tissue is being removed and how much tissue has been removed and is different from indirect or direct visualization used to see the area where tissue may be removed. The Sight Tube 112 is connected to the proximal end of the Inner Shaft 101 on its' distal end and to the Adapter Tube 111 on its' proximal end. The lumen in the Sight Tube 112 is a larger diameter than the Inner Shaft 101, therefore, when the tissue reaches the Sight Tube 112, it slows and adheres to the side of the Sight Tube 112 rather than passing through to the Adapter Tube 111. Alternatively, a filter component (not shown) may be added to prevent tissue from passing through the Sight Tube 112.

The Stop Cock 114 has two positions; in one position it opens the passage between the Sight Tube 112 and the Vacuum Tube (not shown) that connects to the Stop Cock 114 and exits the butt 115 of the Handle Grip 73. When placed in this position, the vacuum is open to the Anvil 40, Inner Shaft 101, and Sight Tube 112 system. When the Stop Cock 114 is in its' second position, the vacuum is shut off to the Anvil 40, Inner Shaft 101, and Sight Tube 112 and the rear luer is open to the Sight tube 112 and Inner Shaft 101 to enable the insertion of a Stylus, endoscope, and dye injection catheters, through the Inner Shaft 101 and Anvil 40.

The Vacuum Tube Luer Fitting 116 connects a conventional Vacuum Tube, (not shown) to the Stop Cock 114 within the grip of the handle. The Vacuum Tube (not shown) extends out of the butt of the handle 115 and connects the device to a vacuum source.

The Trigger Return Spring 117 is connected to a pin 118 in the Handle on its' proximal end and to a pin 119 inserted in the Trigger Shaft 109 on its' distal end. The tensile force is increased on the Trigger Return Spring 117 when the Trigger 110 is actuated, when the Trigger 110 is released, the Trigger Return Spring 117 pulls the Trigger 110 back into position.

The Trigger 110 is actuated by the operator to actuate the Outer Shaft 100 and is connected to the Outer Shaft 100 via the Trigger Shaft 109 and Cutter Grasp 108 mechanism. A pin 119 inserted into the Trigger Shaft 109 slides within a slot on the Trigger 110.

Methods of Treating a Herniated Disc

Embodiments of the present invention further include methods of treating a herniated disc. The methods employ the cutting devices of the present invention to selectively remove nucleus pulposus material from a specific target site. In certain aspects, the target site is a specific site within the nucleus. In other aspects, the specific target site is the site of herniation in which the subject devices directly access and excise nucleus pulposus material at the site of herniation within the fissure. In a particular embodiment, the subject devices are able to enter the nucleus from the side contralateral to the herniation and directly approach the herniation site from within the nucleus. Therefore, the subject devices are able to perform a selective percutaneous discectomy by navigating through the confines of the nucleus to a specific target site.

EXEMPLARY METHODS

It will be apparent to one of skill in the art that the cutting devices of the present invention may be employed in a variety of different protocols for performing a discectomy. As such, the method provided below is exemplary and not to be construed as a limitation.

Example 1

Indirect Visualization

In general, a patient is examined and diagnosed with a herniated disc. Imaging technology such as MRI or an X-ray device is used to locate the position of the herniated disc. An introducer such as a hypodermic needle is provided that is inserted in a patient's body so that its distal end creates a small annular opening leading to the nucleus pulposus. A guide wire is slid into position within and through the introducer lumen so that a distal tip of the guide wire is positioned at the selected location within the nucleus by advancing or retracing the guide wire in the introducer lumen and optionally twisting the proximal end of the guide wire to precisely navigate the guide wire. A plurality of Guide Wires with different curvatures may be provided that enable the operator to navigate to precise locations within the nucleus pulposus.

A small incision is then made in the patient's skin and subcutaneous tissue which facilitates access of a dilator sheath. The introducer is then removed while leaving the Guide Wire in place and the dilator sheath is advanced over the guide wire to dilate the opening from the patient's skin to the intervertebral disc. The dilator sheath abuts the disc but does not penetrate the disc.

Next, a cannula having at least one lumen is slid over the sheath and navigated to the distal most portion of the guide wire within the nucleus and the guide wire and cannula are then removed from the patient and lumen of the cannula.

Alternatively, the cannula may be advanced to abut the disc annulus, the guide wire and dilator are removed from the patient and cannula lumen, and a trocar is advanced through the lumen of the cannula to pierce the disc annulus and gain entry to the nucleus.

A cutting device of the present invention is advanced through the lumen of the cannula. As the cutting device advances, it follows a curved path to the site of disc herniation because the distal portion of the subject device is configured to curve away from the distal end of the cannula towards the posterior wall of the annulus. The distal tip of the cutting device is configured with a Safety Tip 50 to minimize the possibility of piercing the wall of the annulus from the inside.

Figure 7:
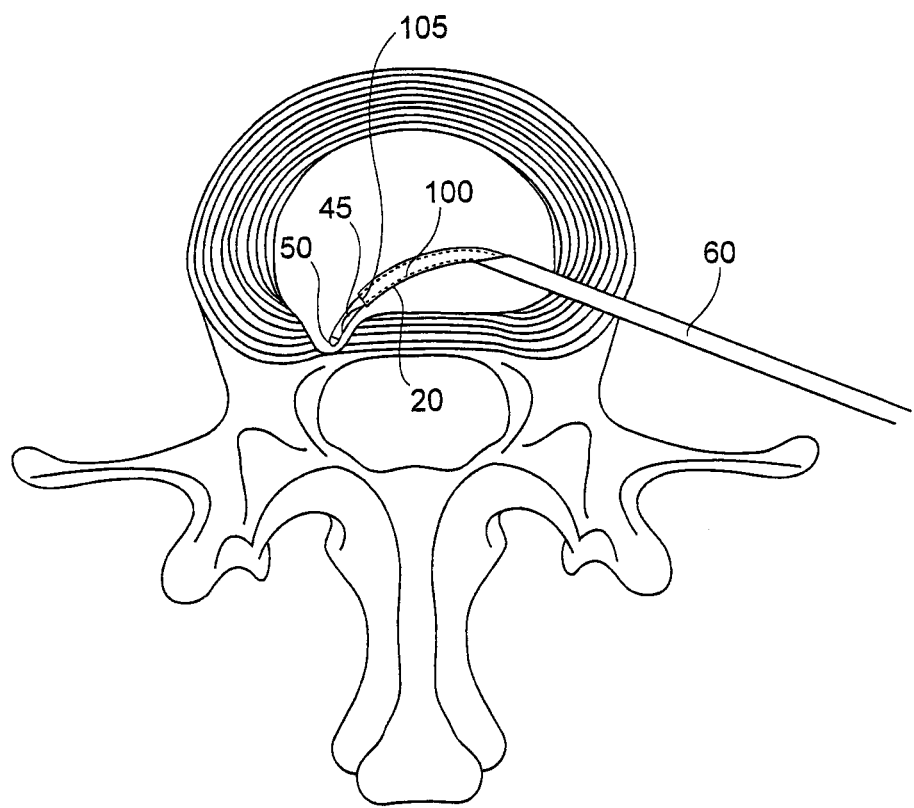
FIG. 7 illustrates an embodiment of the cutting device with a contralateral insertion and now positioned within the confines of the nucleus at a site of herniation.

The subject cutting device will be advanced until the open window of the cutting window (45) is directly positioned at the target site as illustrated in FIG. 7. Markers which can be seen on X-ray may be present at specific locations along the device and at cutting window 45. At different points in time an X-ray image may be taken and used to adjust the position of the window at the herniation. In certain aspects, the target site is a specific site within the nucleus. In other aspects, the specific target site is the specific site within the fissure of herniation. A vacuum may be applied to draw tissue into the open window 45 in the anvil 40 and the outer shaft 100. The Cutter 30 of the subject device will be advanced towards the distal end of the Anvil 40 thereby cutting any nucleus pulposus material present in the open window (45). In some embodiments, the Inner shaft 101 includes a lumen which communicates with a vacuum source that may be applied through the lumen to draw tissue into the cutting window of the anvil. The subject cutting device excises tissue until the disc herniation has been adequately debulked. The subject device is then withdrawn from the cannula and the entry site is closed with a suture or adhesive.

Example 2

In another exemplary embodiment for treating a herniated disc, a guide wire may be guided with fluoroscopic imaging to a position at the specific site of herniation. The guide wire may include markers which can be observed via X-ray and a bevel tip on the distal end and be made of a material having shape memory or elastic characteristics with a curvature at its' distal end. The guide wire may then be used to easily and accurately navigate to the herniation site to create a pathway for subsequent devices to follow to the herniation site. The Guide Wire may then be left in place to serve as a guide to the herniation site or subsequently inserted devices may follow the pathway left by the guide wire. The guide wire may be left in place or removed and the herniation site debulked as described in Example 1.

Example 3

Direct Visualization

In general, a patient is examined and diagnosed with a herniated disc. Although direct visualization is to be used, imaging technology such as MRI or an X-ray device may still be used to locate the position of the herniated disc and the position may be marked on the patient.

An introducer such as a hypodermic needle is provided that is inserted in a patient's body so that its distal end creates an annular opening leading to the nucleus pulposus. A guide wire is slid into position within and through the introducer lumen so that a distal tip of the guide wire is positioned at the selected location within the nucleus by advancing or retracing the guide wire in the introducer lumen and optionally twisting the proximal end of the guide wire to precisely navigate the guide wire.

A small incision is then made in the patient's skin and subcutaneous tissue which facilitates access of a dilator sheath. The introducer is then removed and the dilator sheath is advanced over the guide wire to dilate the incision from the patient's skin to the intervertebral disc. The dilator sheath abuts the disc but does not penetrate the disc.

Next, a cannula having at least one lumen is slid over the sheath and navigated to the distal most portion of the guide wire within the nucleus and the guide wire and cannula are removed from the lumen of the cannula. Alternatively, the cannula may be advanced to abut the disc annulus, the guide wire and dilator are removed from the lumen, and a trocar is advanced through the lumen of the cannula to pierce the disc annulus and gain entry to the nucleus. Direct visualization is used to position the cutting component at the herniation.

A cutting device of the present invention is advanced through the lumen of the cannula. As the cutting device advances, it follows a curved path to the site of disc herniation because the distal portion of the subject device is configured to curve away from the distal end of the cannula towards the posterior wall of the annulus. The distal tip of the cutting device is configured to minimize the possibility of piercing the wall of the annulus from the inside.

The subject cutting device will be advanced using direct visualization until the open window of the cutting window (45) is directly positioned at the target site as illustrated in FIG. 7. In certain aspects, the target site is a specific site within the nucleus. In other aspects, the specific target site is the specific site of herniation within the fissure. A vacuum may be applied to remove blood or material blocking direct visualization. The vacuum is then used to draw tissue into the open window in the anvil. The Cutter 30 of the subject device will be advanced to slide towards the distal end of the Anvil 40, thereby cutting any nucleus pulposus material present in the open window (45). Direct visualization can be used to determine if the herniation has been removed. In some embodiments, the flexible shaft includes a lumen which communicates with a vacuum source to draw tissue into the cutting window of the anvil. The subject cutting device excises tissue until the disc herniation has been adequately debulked. The subject device is then withdrawn from the cannula and the entry site is closed with a suture or adhesive.

Example 4

In another exemplary embodiment for treating a herniated disc, a guide wire is positioned at the specific site of herniation using direct visualization. The guide wire may include a bevel tip on the distal end and be made of a material having shape memory or elastic characteristics. The guide wire may then be used to easily and accurately navigate to the herniation site to create a pathway for subsequent devices to follow to the herniation site. The Guide Wire may then be left in place to serve as a guide to the herniation site or subsequently inserted devices may follow the pathway left by the guide wire. The guide wire may be left in place or removed and the herniation site debulked as described in Example 3.

Use with Jig

In certain embodiments, a jig is employed to hold the cannula in place on the patient's skin. By using a jig, the patient is able to move during the procedure while the cannula and cutting device remains in place. Aspects of this embodiment include attaching the jig to the patient or the bed via an adhesive or screw. In this embodiment, calculations are performed to determine reference points to define the proper plane in which the cannula should be positioned to allow for access to the posterior wall of the annulus within the confines of the nucleus. Methods for employing a jig in surgical methods are provided in U.S. Pat. Nos. 5,251,127, 5,305,203, 5,086,401, 5,299,288 and 5,408,409, the disclosures of which are herein incorporated. In a particular embodiment, the jig may be attached to the cannula or cutting device after they are in position within the disc and the proper position of the cannula has been defined.

A medical practitioner may require or find it useful to precisely position the cutting device of the invention when performing surgery on a patient. To do such patient data may be developed which identifies the position and orientation of a particular target site such as the site of herniation which is to be removed. The position and orientation of the cutting device of the invention is sensed and instrument data is developed from the sensing. The patient data is converted to objective signals which may be displayed on a video display. The instrument data may be converted to instrument signals for presenting the position and orientation of the cutting device of the invention. Accordingly, by watching the displays the medical practitioner may be aided in the manipulation and maneuvering of the distal end of the cutting device of the invention in order to move it into precise position beside the site of herniation. Methodologies and devices which aid in sensing and obtaining such data and positioning the instrument are described in publications such as U.S. Pat. No. 5,251,127 issued Oct. 5, 1993.

Kits

Also provided are kits for practicing the present methods. The present kits may vary greatly in regards to the components that are included in the kit. The present kits at least include a subject cutting device for use in practicing the present methods.

The present kits may also include radiopaque dye to be injected into the operative site for visualization purposes. For example, the subject kits may include dilute barium sulphate solution, bismuth trioxide, iodine, iodide, titanium oxide, zirconium oxide, metals such as gold, platinum, silver, tantalum, niobium, stainless steel, and combinations thereof.

In certain embodiments, the subject kits may additionally include a medicament to be delivered within the disc. For example, the kits may include a pharmaceutical agent, chemonucleolytic enzymes, hydrogel substances, osteoinductive substances, chondrocyte-inductive substances, sealants, collagen, fibrinogen, thrombin and combinations thereof.

In some embodiments, the subject kits may further include a liquid jet device and a liquid solution to be delivered into the nucleus. For example, the kits may include saline solution or sterile water.

In a particular embodiment, the subject devices may include stylets and control wires for adjusting the curvature of the subject devices. Aspects of this embodiment include 2, 3, 4 or more stylets that have degrees of curvatures relative to each other which allow for the subject cutting devices to accordingly have varying ranges of curvatures.

In a particular embodiment, the kits may include a jig to hold the cannula and/or the cutting devices in a fixed position relative to the patient.

In a particular embodiment, the kits may include the components required to gain access to the disk such as the Guide Wire, Dilator, Cannula, and Trocar.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A system for performing a discectomy comprising:
   a flexible shaft having a proximal end portion, a distal end portion, and a lumen extending there between, wherein the shaft is adapted for insertion into a cannula having a proximal end and a distal end wherein the distal end portion of the shaft is configured to advance from a distal end of the cannula and into an intervertebral disc and substantially along a posterior wall of an intervertebral disc and the distal end portion of the shaft has a predetermined curvature which causes at least a portion of the distal end portion of the shaft to curve upon exiting the distal end of the cannula, such that the shaft can be navigated toward a herniation site located at a posterior wall of the disc to cut tissue; and
   a mechanical cutting mechanism positioned on a side of the distal end portion of the shaft facing the direction of curvature of the shaft and in fluid communication with the lumen of the shaft, the cutting mechanism configured to cut in the direction of the curvature.

2. The system of claim 1, wherein a distal end portion of the shaft is configured to advance from a distal end of the cannula in a curved path which substantially matches the predetermined curvature of the shaft.

3. The system of claim 1, wherein the shaft is configured to navigate directly toward the herniation site in a substantially curved path.

4. The system of claim 1, wherein the shaft comprises an elastic or shape memory material.

5. The system of claim 4, wherein the material is selected from the group consisting of Pebax, Nylon, Nitinol, PVC, Stainless Steel wire, and Nitinol wire.

6. The system of claim 1, wherein the cutting mechanism is configured to cut away tissue causing the herniation site.

7. The system of claim 1, further comprising a deflectable stylus inserted within the shaft, wherein the stylus is curved to create a desired degree of curvature in the shaft.

8. The system of claim 1, wherein the shaft comprises a lumen for delivering a fluid to facilitate evacuation of the excised disc tissue through the cutting window.

9. The system of claim 1, wherein the shaft comprises a lumen connected to a vacuum source for evacuation of fluid or tissue.

10. The system of claim 1, further comprising a collection chamber in fluid connection with the shaft and configured to collect material excised by the cutting mechanism and allow for visualization of the collected material in the chamber.

11. The system of claim 1, wherein the shaft comprises an outer shaft and an inner shaft inserted within the outer shaft and comprising the cutting mechanism, wherein the cutting mechanism comprises a cutting window and a cutting ring which interact to cut when the inner and outer shafts are moved relative to each other.

12. The system of claim 1, further comprising a control wire connected to and extending along a length of the shaft.

13. The system of claim 1, wherein the shaft is configured for insertion into an intervertebral disc at a position located contralateral to the herniation site.

14. The system of claim 1, wherein the shaft has a predetermined curvature and the distal end portion of the shaft is configured to begin reverting to its predetermined curvature after exiting the cannula to position at least a portion of the distal end portion of the shaft near the herniation site.

15. The system of claim 1, wherein the shaft has a predetermined curvature and the distal end portion of the shaft is configured to substantially assume its predetermined curvature after exiting the cannula to position at least a portion of the distal end portion of the shaft near the herniation site.

16. The system of claim 1, wherein the shaft is configured to navigate within the disc along a plane of the disc in a single plane of movement.

17. The system of claim 1, wherein the shaft comprises a lumen connected to a vacuum source for suctioning tissue causing the herniation into the cutting mechanism such that the cutting mechanism can cut the suctioned tissue.

18. The system of claim 1, wherein the shaft is configured to be steered by adjusting a depth of the cannula within the disc.

19. A system for performing a discectomy comprising:
a flexible shaft having a proximal end portion, a distal end portion having a predetermined curvature, and a lumen extending there between, where the shaft is adapted for insertion into a cannula having a proximal end and a distal end, wherein the distal end portion of the shaft is configured to advance from the distal end of the cannula and into an intervertebral disc and allow its predetermined curvature to cause at least a portion of the distal end portion of the shaft to curve upon exiting the distal end of the cannula to position at least a portion of the distal end portion of the shaft near a herniation site to cut tissue; and
a mechanical cutting mechanism positioned on a side of the distal end portion of the shaft facing the direction of curvature of the shaft and in fluid communication with the lumen of the shaft, the cutting mechanism configured to cut in the direction of the curvature.

20. The system of claim 19, wherein the shaft is configured to navigate directly toward the herniation site in a substantially curved path.

21. The system of claim 19, wherein the shaft comprises an elastic or shape memory material.

22. The system of claim 21, wherein the material is selected from the group consisting of Pebax, Nylon, Nitinol, PVC, Stainless Steel wire, and Nitinol wire.

23. The system of claim 19, further comprising a deflectable stylus inserted within the shaft, wherein the stylus is curved to create a desired degree of curvature in the shaft.

24. The system of claim 19, wherein the shaft comprises a lumen for delivering a fluid to facilitate evacuation of the excised disc tissue through the cutting window.

25. The system of claim 19, wherein the shaft comprises a lumen connected to a vacuum source for evacuation of fluid or tissue.

26. The system of claim 19, further comprising a collection chamber in fluid connection with the shaft and configured to collect material excised by the cutting mechanism and allow for visualization of the collected material in the chamber.

27. The system of claim 19, wherein the shaft is configured for insertion into an intervertebral disc at a position located contralateral to the herniation site.

28. The system of claim 19, wherein the distal end portion of the shaft is configured to begin reverting to its predetermined curvature after exiting the cannula to position at least a portion of the distal end portion of the shaft near the herniation site.

29. The system of claim 19, wherein the distal end portion of the shaft is configured to substantially assume its predetermined curvature after exiting the cannula to position at least a portion of the distal end portion of the shaft near the herniation site.

30. The system of claim 19, wherein the distal end portion of the shaft is configured to advance from a distal end of the cannula in a curved path which substantially matches the predetermined curvature of the shaft.

31. The system of claim 19, wherein the shaft is configured to navigate within the disc along a plane of the disc in a single plane of movement.

32. The system of claim 19, wherein the shaft comprises a lumen connected to a vacuum source for suctioning tissue causing the herniation into the cutting mechanism such that the cutting mechanism can cut the suctioned tissue.

33. The system of claim 19, wherein the shaft is configured to be steered by adjusting a depth of the cannula within the disc.

34. The system of claim 1, wherein the shaft is configured to cut tissue at and/or near the herniation site while retaining tissue in the remainder of the disc.

35. The system of claim 1, wherein the shaft does not cut tissue until the cutting mechanism is in position near the herniation site.

* * * * *